(12) United States Patent
Giaccia et al.

(10) Patent No.: US 9,074,192 B2
(45) Date of Patent: *Jul. 7, 2015

(54) INHIBITION OF AXL SIGNALING IN ANTI-METASTATIC THERAPY

(75) Inventors: Amato J. Giaccia, Stanford, CA (US); Erinn Bruno Rankin, Waltham, MA (US); Jennifer R. Cochran, Stanford, CA (US); Douglas Jones, Cambridge, MA (US); Mihalis Kariolis, Stanford, CA (US); Katherine Fuh, Palo Alto, CA (US); Yu Miao, Sunnyvale, CA (US)

(73) Assignee: THE BOARD OF TRUSTEES OF THE LELAND STANFORD JUNIOR UNIVERSITY, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/595,936

(22) Filed: Aug. 27, 2012

(65) Prior Publication Data

US 2013/0108644 A1    May 2, 2013

Related U.S. Application Data

(63) Continuation-in-part of application No. 13/554,954, filed on Jul. 20, 2012, now Pat. No. 8,618,254, which is a continuation of application No. PCT/US2011/022125, filed on Jan. 21, 2011.

(60) Provisional application No. 61/336,478, filed on Jan. 22, 2010.

(51) Int. Cl.
| | |
|---|---|
| C07K 14/705 | (2006.01) |
| C12N 9/12 | (2006.01) |
| A61K 38/45 | (2006.01) |
| C07K 16/22 | (2006.01) |
| A61K 45/06 | (2006.01) |
| C07K 14/71 | (2006.01) |

(52) U.S. Cl.
CPC . *C12N 9/12* (2013.01); *A61K 38/45* (2013.01); *C07K 16/22* (2013.01); *A61K 45/06* (2013.01); *C07K 2319/30* (2013.01); *C07K 14/71* (2013.01)

(58) Field of Classification Search
CPC .......................... C07K 14/705; C07K 2319/30
See application file for complete search history.

(56) References Cited

U.S. PATENT DOCUMENTS

| 5,538,861 | A  | 7/1996 | Schneider et al. |
|---|---|---|---|
| 6,096,527 | A  | 8/2000 | Godowski et al. |
| 6,737,056 | B1 | 5/2004 | Presta |
| 7,709,482 | B2 | 5/2010 | Goff et al. |
| 8,168,415 | B2 | 5/2012 | Graham et al. |
| 2005/0186571 | A1 | 8/2005 | Ullrich et al. |
| 2007/0128200 | A1 | 6/2007 | Yang et al. |
| 2009/0042826 | A1 | 2/2009 | Mor et al. |
| 2009/0087431 | A1 | 4/2009 | Yaworsky et al. |
| 2010/0266604 | A1 | 10/2010 | Rothlin et al. |
| 2013/0189254 | A1* | 7/2013 | O'Connor et al. ......... 424/134.1 |

FOREIGN PATENT DOCUMENTS

| EP | 1897940 | 3/2008 |
|---|---|---|
| JP | 2005-278631 A | 10/2005 |
| JP | 2005-532805 T | 11/2005 |
| WO | 2004/092735 | 10/2004 |
| WO | 2004/108748 | 12/2004 |
| WO | 2008098139 | 8/2008 |
| WO | 2009/005813 | 1/2009 |
| WO | 2011/014457 | 2/2011 |
| WO | 2011091305 | 7/2011 |
| WO | 2011/159980 | 12/2011 |

OTHER PUBLICATIONS

Altomare; et al. "AKT and mTOR phosphorylation is frequently detected in ovarian cancer and can be targeted to disrupt ovarian tumor cell growth", Oncogene (Jul. 2004), 23(34):5853-5857.
Angelillo-Scherrer; et al. "Deficiency or inhibition of Gas6 causes platelet dysfunction and protects mice against thrombosis", Nat Med (Feb. 2001), 7(2):215-221.
Armstrong; et al. "Intraperitoneal cisplatin and paclitaxel in ovarian cancer", N. Engl J Med (Jan. 2006), 354(1):34-43.
Berclaz; et al. "Estrogen dependent expression of the receptor tyrosine kinase axl in normal and malignant human breast", Ann Oncol (Jun. 2001), 12(6):819-824.
Bonome; et al. "Expression profiling of serous low malignant potential, low-grade, and high-grade tumors of the ovary", Cancer Res (Nov. 2005), 65(22):10602-10612.
Cheng; et al. "AKT2, a putative oncogene encoding a member of a subfamily of protein-serine/threonine kinases, is amplified in human ovarian carcinomas", Proc Natl Acad Sci U S A (Oct. 1992), 89(19): 9267-9271.
Choi; et al. "Gonadotropins activate proteolysis and increase invasion through protein kinase A and phosphatidylinositol 3-kinase pathways in human epithelial ovarian cancer cells", Cancer Res (Apr. 2006), 66(7):3912-3920.
Egeblad; et al. "New functions for the matrix metalloproteinases in cancer progression" Nat Rev Cancer (Mar. 2002), 2(3):161-174.
Erler; et al. "Lysyl oxidase is essential for hypoxia-induced metastasis", Nature (Apr. 2006), 440(7088):1222-1226.

(Continued)

*Primary Examiner* — Sheela J Huff
*Assistant Examiner* — Jessica H Roark
(74) *Attorney, Agent, or Firm* — Bozicevic, Field & Francis LLP; Pamela J. Sherwood

(57) ABSTRACT

Compositions and methods are provided for alleviating cancer in a mammal by administering a therapeutic dose of a pharmaceutical composition that inhibits activity of AXL protein activity, for example by competitive or non-competitive inhibition of the binding interaction between AXL and its ligand GAS6.

7 Claims, 20 Drawing Sheets
(11 of 20 Drawing Sheet(s) Filed in Color)

(56) References Cited

OTHER PUBLICATIONS

Fridell; et al. "GAS6 induces Axl-mediated chemotaxis of vascular smooth muscle cells", J Biol Chem (Mar. 1998), 273(12):7123-7126.
Goruppi; et al. "Gas6-mediated survival in NIH3T3 cells activates stress signalling cascade and is independent of Ras", Oncogene (Jul. 1999), 18(29):4224-4236.
Guo; et al. "Increased staining for phosphorylated AKT and nuclear factor-kappaB p65 and their relationship with prognosis in epithelial ovarian cancer", Pathol Int (Dec. 2008), 58(12):749-756.
Holland; et al. "Multiple roles for the receptor tyrosine kinase axl in tumor formation", Cancer Res (Oct. 2005), 65(20):9294-9303.
Hua; et al."Estrogen and progestin regulate metastasis through the PI3K/AKT pathway in human ovarian cancer", Int J Oncol (Nov. 2008), 33(5):959-967.
Hutterer; et al."Axl and growtharrest-specific gene 6 are frequently overexpressed in human gliomas and predict poor prognosis in patients with glioblastoma multiforme", Clin Cancer Res (Jan. 2008), 14(1):130-138.
Janssen; et al. "A novel putative tyrosine kinase receptor with oncogenic potential", Oncogene (Nov. 1991), 6(11):2113-2120.
Kenny; et al. "The initial steps of ovarian cancer cell metastasis are mediated by MMP-2 cleavage of vitronectin and fibronecti", J Clin Invest (Apr. 2008), 118(4): 1367-1379.
Koorstra; et al. "The Axl receptor tyrosine kinase confers an adverse prognostic influence in pancreatic cancer and represents a new therapeutic target", Cancer Biol Ther (Apr. 2009), 8(7):618-626.
Kuhnert; et al. "Soluble receptor-mediated selective inhibition of VEGFR and PDGFRbeta signaling during physiologic and tumor angiogenesis", Proc Natl Acad Sci U S A (Jul. 2008), 105(29):10185-10190.
Kuo; et al. "Comparative evaluation of the antitumor activity of antiangiogenic proteins delivered by gene transfer", Proc Natl Acad Sci U S A (Apr. 2001), 98(8):4605-4610.
Lancaster; et al. "Identification of genes associated with ovarian cancer metastasis using microarray expression analysis", Int J Gynecol Cancer (Sep.-Oct. 2006), 16(5):1733-1745.
Lengyel; et al. "Expression of latent matrix metalloproteinase 9 (MMP-9) predicts survival in advanced ovarian cancer", Gynecol Oncol (Aug. 2001), 82(2):291-298.
Li; et al. "Axl as a potential therapeutic target in cancer: role of Axl in tumor growth, metastasis and angiogenesis", Oncogene (Oct. 2009), 28(39):3442-3455.
Linger; et al. "TAM receptor tyrosine kinases: biologic functions, signaling, and potential therapeutic targeting in human cancer", Adv Cancer Res (2008), 100:35-83.
Liu; et al. "AKT2, a member of the protein kinase B family, is activated by growth factors, v-Ha-ras, and v-src through phosphatidylinositol 3-kinase in human ovarian epithelial cancer cells", Cancer Res, (Jul. 1998), 58(14):2973-2977.
Lu; et al. "Homeostatic regulation of the immune system by receptor tyrosine kinases of the Tyro 3 family", Science (Jul. 2001), 293(5528):306-311.
Martin; et al. "Management of recurrent ovarian carcinoma: current status and future directions", Semin Oncol (Apr. 2009), 36(2):112-125.
McCloskey; et al. "GAS6 mediates adhesion of cells expressing the receptor tyrosine kinase Axl", J Biol Chem (Sep. 1997), 272(37):23285-23291.
Mills; et al. "The role of genetic abnormalities of PTEN and the phosphatidylinositol 3-kinase pathway in breast and ovarian tumorigenesis, prognosis, and therapy", Semin Oncol (Oct. 2001), 28(5 Suppl 16):125-141.
Nakayama; et al. "Amplicon profiles in ovarian serous carcinomas", Int J Cancer (Jun. 2007), 120(12):2613-2617.
Naora; et al. "Ovarian cancer metastasis: integrating insights from disparate model organisms", Nat Rev Cancer (May 2005), 5(5):355-366.
Nielsen-Preiss; et al. "Adhesion-related kinase induction of migration requires phosphatidylinositol-3-kinase and ras stimulation of rac activity in immortalized gonadotropin-releasing hormone neuronal cells", Endocrinology (Jun. 2007), 148(6):2806-2814.
O'Bryan; et al."axl, a transforming gene isolated from primary human myeloid leukemia cells, encodes a novel receptor tyrosine kinase", Mol Cell Biol (Oct. 1991), 11(10): 5016-5031.
O'Bryan; et al. "The transforming receptor tyrosine kinase, Axl, is post-translationally regulated by proteolytic cleavage", J Biol Chem (Jan. 1995), 270(2):551-557.
Perigny; et al. "Role of immunohistochemical overexpression of matrix metalloproteinases MMP-2 and MMP-11 in the prognosis of death by ovarian cancer", Am J Clin Pathol (Feb. 2008), 129(2):226-231.
Rankin; et al. "Renal cyst development in mice with conditional inactivation of the von Hippel-Lindau tumor suppressor", Cancer Res (Mar. 2006), 66(5):2576-2583.
Sahai; et al. "Illuminating the metastatic process", Nat Rev Cancer (Oct. 2007), 7(10):737-749.
Sasaki; et al. "Structural basis for Gas6-Axl signalling", EMBO J (Jan. 2006), 25(1):80-87.
Satpathy; et al. "Tissue transglutaminase regulates matrix metalloproteinase-2 in ovarian cancer by modulating cAMP-response element-binding protein activity", J Biol Chem (Jun. 2009), 284(23):15390-15399.
Shieh; et al. "Expression of Axl in Lung Adenocarcinoma and Correlation with Tumor Progression", Neoplasia (Dec. 2005), 7(12): 1058-1064.
Sun; et al. "Coexpression of Gas6/Axl in human ovarian cancers", Oncology (2004), 66(6):450-457.
Sutphin; et al. "Targeting the loss of the von Hippel-Lindau tumor suppressor gene in renal cell carcinoma cells", Cancer Res (Jun. 2007), 67(12):5896-5905.
Tai; et al. "Axl promotes cell invasion by inducing MMP-9 activity through activation of NF-kappaB and Brg-1", Oncogene (Jul. 2008), 27(29):4044-4055.
Tan; et al. "Mechanisms of transcoelomic metastasis in ovarian cancer", Lancet Oncol (Nov. 2006), 7(11):925-934.
Vajkoczy; et al. "Dominant-negative inhibition of the Axl receptor tyrosine kinase suppresses brain tumor cell growth and invasion and prolongs survival", Proc Natl Acad Sci U S A (Apr. 2006), 103(15):5799-5804.
Yoneda; et al. "Expression of angiogenesis-related genes and progression of human ovarian carcinomas in nude mice", J Natl Cancer Inst (Mar. 2009), 90(6):447-454.
Zhang; et al. "AXL is a potential target for therapeutic intervention in breast cancer progression", Cancer Res (Mar. 2008), 68(6):1905-1915.
Patel: et al., "Engineering an APRIL-specific B Cell Maturation Antigen", The Journal of Biological Chemistry (Apr. 2004), 279(16):16727-16735.
Cerchia; et al., "Targeting Axl with an high-affinity inhibitory aptamer", Mol Ther (Dec. 2012), 20(12):2291-2303.
Healy; et al., "Gas 6 promotes Axl-mediated survival in pulmonary endothelfal cells", Am J Physiol Lung Cell Mol Physiol (Jun. 2001), 280(6):L1273-1281.
Mark; et al., "Characterization of Gas6, a Member of the Superfamily of G Domain-containing Proteins, as a Ligand for Rse and Axl", J Biol Chem (Apr. 1996), 271(16):9785-9789.
Nagata; et al., "Identification of the product of growth arrest-specific gene 6 as a common ligand for Axl, Sky, and Mer receptor tyrosine kinases", J Biol Chem (Nov. 1996), 271(47):30022-30027.
"Quantikine ELISA. Mouse Gas6 Immunoassay", R&D Systems, Inc. (Apr. 2013), Catalog No. MGAS60, 12 pgs., Retrieved from the Internet on Mar. 18, 2014, http://www.mdsystems.com/pdf/MGAS60.pdf.
Sawabu, Tateo et al., Growth Arrest-Specific Gene 6 and Axl Signaling Enhances Gastric Cancer Cell Survival via Akt Pathway, 2007, pp. 155-164, vol. 46, Molecular Carcinogenesis.

* cited by examiner

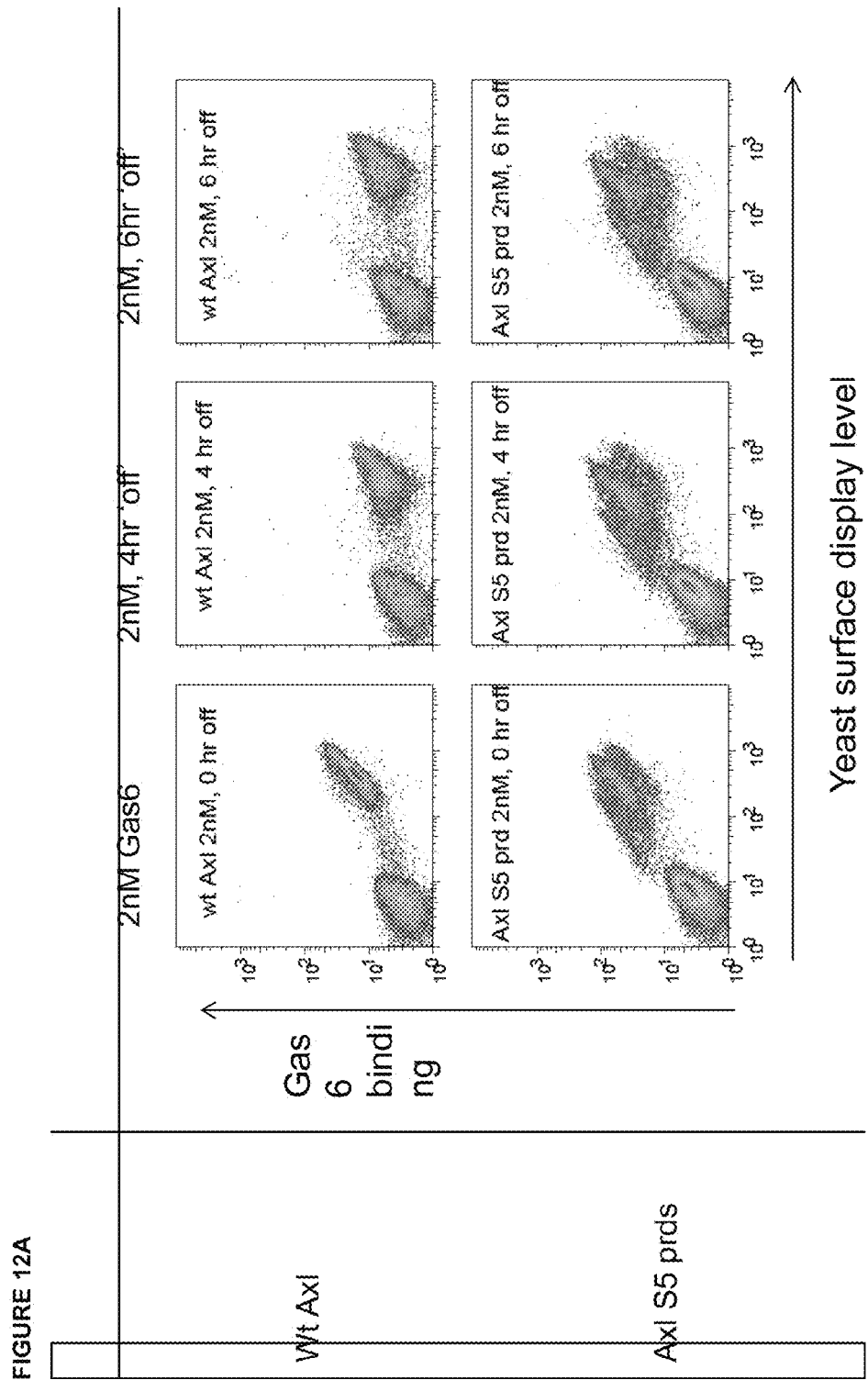

FIGURE 18

| Axi variant | Dose (mg/kg) | Radiance [x10³] (p/sec/cm²/sr) | | | | | | | | | | | | |
|---|---|---|---|---|---|---|---|---|---|---|---|---|---|---|
| | | Mouse 1 | Mouse 2 | Mouse 3 | Mouse 4 | Mouse 5 | Mouse 6 | Mouse 7 | Mouse 8 | Mouse 9 | Mouse 10 | Mouse 11 | Mouse 12 | Average | SEM |
| S6-1 | 1 | 3060 | 15600† | 2160 | 1440 | 1140 | 525 | 2160 | 2560 | 1040 | 6450 | 941 | 986 | | |
| | | 1160 | 2710 | 823 | 59.6 | 1450 | 554 | 83.7 | 1120 | 6.42 | 1290 | 242 | 264 | 814 | 228 |
| | | 67.5 | 424 | 663 | 451 | 682 | 60.2 | 773 | 259 | 801 | 416 | 2190† | 354 | | |

† Outliers, not included in mean or SEM calculations

FIGURE 19

| Axl variant | Dose (mg/kg) | Relative metastatic burden | | | | | | | | | | | | |
|---|---|---|---|---|---|---|---|---|---|---|---|---|---|---|
| | | Mouse 1 | Mouse 2 | Mouse 3 | Mouse 4 | Mouse 5 | Mouse 6 | Mouse 7 | Mouse 8 | Mouse 9 | Mouse 10 | Mouse 11 | Mouse 12 | Average | SEM |
| S6-1 | 1 | 0 | 0 | 75.53 | n.a. | 82.41 | 0 | 53.56 | 51.33 | 0 | 62.77 | 82.12 | 0 | 33.98 | 10.60 | n.a. = DNA unrecoverable from lung tissue

INHIBITION OF AXL SIGNALING IN ANTI-METASTATIC THERAPY

The application is a continuation-in-part of U.S. application Ser. No. 13/554,954 filed on Jul. 20, 2012, which is a continuation of International Application No. PCT/US2011/022125 filed on Jan. 21, 2011, which claims priority from U.S. Provisional Application No. 61/336,478 filed on Jan. 22, 2010, the contents of which are expressly incorporated herein by reference.

FIELD OF THE INVENTION

The present invention relates to tumor invasion and metastasis, e.g., treatments or diagnoses of tumor invasion or metastasis via pathways related to AXL and/or GAS6

BACKGROUND OF THE INVENTION

Invasion and metastasis are the most insidious and life-threatening aspects of cancer. While tumors with minimal or no invasion may be successfully removed, once the neoplasm becomes invasive, it can disseminate via the lymphatics and/or vascular channels to multiple sites, and complete removal becomes very difficult. Invasion and metastases kill hosts through two processes: local invasion and distant organ colonization and injury. Local invasion can compromise the function of involved tissues by local compression, local destruction, or prevention of normal organ function. The most significant turning point in cancer, however, is the establishment of distant metastasis. The patient can no longer be cured by local therapy alone at this point.

The process of metastasis is a cascade of linked sequential steps involving multiple host-tumor interactions. This complex process requires the cells to enter into the vascular or lymphatic circulation, arrest at a distant vascular or lymphatic bed, actively extravasate into the organ interstitium and parenchyma, and proliferate as a secondary colony. Metastatic potential is influenced by the local microenvironment, angiogenesis, stroma-tumor interactions, elaboration of cytokines by the local tissue, and by the molecular phenotype of the tumor and host cells.

Local microinvasion can occur early, even though distant dissemination may not be evident or may not yet have begun. Tumor cells penetrate the epithelial basement membrane and enter the underlying interstitial stroma during the transition from in situ to invasive carcinoma. Once the tumor cells invade the underlying stroma, they gain access to the lymphatics and blood vessels for distant dissemination while releasing matrix fragments and growth factors. General and widespread changes occur in the organization, distribution, and quantity of the epithelial basement membrane during the transition from benign to invasive carcinoma.

Therapeutic efforts in cancer prevention and treatment are being focused at the level of signaling pathways or selective modulatory proteins. Protein kinase activities, calcium homeostasis, and oncoprotein activation are driving signals and therefore may be key regulatory sites for therapeutic intervention. Kinases in signaling pathways regulating invasion and angiogenesis may be important regulators of metastasis. One of the largest classes of biochemical molecular targets is the family of receptor tyrosine kinases (RTKs). The most common receptor tyrosine kinase molecular targets to date are the EGF and vascular endothelial growth factor (VEGF) receptors. Newer kinase molecular targets include the type III RTK family of c-kit, and abl. Inhibitors of these molecules have been administered in combination with classic chemotherapeutics.

Metastases ultimately are responsible for much of the suffering and mortality from cancer. A need exists to identify and target molecular and functional markers that identify metastatic cancer cells and to generate reagents for their specific inhibition.

Publications in this field include, inter alia, Li et al. Oncogene. (2009) 28(39):3442-55; United States Patent Application, 20050186571 by Ullrich et al.; United States Patent Application 20080293733 by Bearss et al.; Sun et al. Oncology. 2004; 66(6):450-7; Gustafsson et al. Clin Cancer Res. (2009) 15(14):4742-9; Wimmel et al. Eur J Cancer. 2001 37(17):2264-74; Koorstra et al. Cancer Biol Ther. 2009 8(7): 618-26; Tai et al. Oncogene. (2008) 27(29):4044-55

The receptor tyrosine kinase AXL (also known as Ufo and Tyro7) belongs to a family of tyrosine receptors that includes Tyro3 (Sky) and Mer (Tyro12). A common ligand for AXL family is GAS6 (Growth arrest-specific protein 6). Human AXL is a 2,682-bp open reading frame capable of directing the synthesis of an 894-amino acid polypeptide. Two variant mRNAs have been characterized, transcript variant 1 may be accessed at Genbank, NM_021913.3 and transcript variant 2 may be accessed at NM_001699.4. The polypeptide sequence of the native protein is provided as SEQ ID NO:1, and specific reference may be made to the sequence with respect to amino acid modifications. Important cellular functions of GAS6/AXL include cell adhesion, migration, phagocytosis, and inhibition of apoptosis. GAS6 and AXL family receptors are highly regulated in a tissue and disease specific manner.

AXL is characterized by a unique molecular structure, in that the intracellular region has the typical structure of a receptor tyrosine kinase and the extracellular domain contains fibronectin III and Ig motifs similar to cadherin-type adhesion molecules. During development, AXL is expressed in various organs, including the brain, suggesting that this RTK is involved in mesenchymal and neural development. In the adult, AXL expression is low but returns to high expression levels in a variety of tumors. GAS6 is, so far, the single, activating ligand for AXL.

Receptor tyrosine kinases (RTK) are generally activated by ligands that promote receptor dimerisation and, in turn, autophosphorylation of tyrosine residues within the cytosolic domain. Binding of signaling proteins to these phosphorylated tyrosine residues then leads to downstream signaling. AXL family RTKs are unique in that they are activated by GAS6, a member of the vitamin K-dependent protein family that resembles blood coagulation factors rather than typical growth factors.

SUMMARY OF THE INVENTION

The present invention is based in part on the discovery that AXL and/or GAS6 related pathways are related to tumor invasion and/or metastasis. Accordingly, the present invention provides compositions and methods useful for treating tumor invasion and/or metastasis, e.g., via inhibition of AXL and/or GAS6 related pathways. In addition, the present invention provides reagents and methods useful for determining the susceptibility or likelihood of a tumor to become invasive and/or metastatic, e.g., via detecting the level of activity of AXL and/or GAS6.

In one embodiment, the present invention provides soluble AXL variant polypeptides, wherein said polypeptide lacks the AXL transmembrane domain, and optionally intracellular domain and comprises at least one amino acid modification relative to the wild-type AXL sequence, and wherein said change increases the affinity of the AXL polypeptide binding to GAS6. In some embodiments, the soluble AXL variant polypeptide comprises at least one amino acid modification within a region selected from the group consisting of 1) between 15-50, 2) between 60-120, and 3) between 125-135 of the wild-type AXL sequence (SEQ ID NO: 1). In some other embodiments, the soluble AXL variant polypeptide comprises at least one amino acid modification at position 19, 23, 26, 27, 32, 33, 38, 44, 61, 65, 72, 74, 78, 79, 86, 87, 88, 90, 92, 97, 98, 105, 109, 112, 113, 116, 118, 127 or 129 of the wild-type AXL sequence (SEQ ID NO: 1) or a combination thereof. In some other embodiments, the soluble AXL variant polypeptide comprises at least one amino acid modification selected from the group consisting of 1) A19T, 2) T23M, 3) E26G, 4) E27G or E27K, 5) G32S, 6) N33S, 7) T38I, 8) T44A, 9) H61Y, 10) D65N, 11) A72V, 12) S74N, 13) Q78E, 14) V79M, 15) Q86R, 16) D87G, 17) D88N, 18) I90M or I90V, 19) V92A, V92G or V92D, 20) I97R, 21) T98A or T98P, 22) T105M, 23) Q109R, 24) V112A, 25) F113L, 26) H116R, 27) T118A, 28) G127R or G127E, and 29) E129K and combinations and conservative equivalents thereof.

In yet some other embodiments, the soluble AXL variant polypeptide comprises amino acid changes relative to the wild-type AXL sequence (SEQ ID NO: 1) at the following positions: (a) glycine 32; (b) aspartic acid 87; (c) valine 92; and (d) glycine 127. In yet some other embodiments, the soluble AXL variant polypeptide comprises amino acid changes relative to the wild-type AXL sequence (SEQ ID NO: 1) at the following positions: (a) aspartic acid 87 and (b) valine 92. In yet some other embodiments, the soluble AXL variant polypeptide comprises amino acid changes relative to the wild-type AXL sequence (SEQ ID NO: 1) at the following positions: (a) glycine 32; (b) aspartic acid 87; (c) valine 92; (d) glycine 127 and (e) alanine 72. In yet some other embodiments, the soluble AXL variant polypeptide comprises amino acid changes relative to the wild-type AXL sequence (SEQ ID NO: 1) at the following position: alanine 72. In yet some other embodiments, the soluble AXL variant polypeptide contains glycine 32 residue replaced with a serine residue, aspartic acid 87 residue replaced with a glycine residue, valine 92 residue replaced with an alanine residue, or glycine 127 residue replaced with an arginine residue or a combination or conservative equivalent thereof. In yet some other embodiments, the soluble AXL variant polypeptide contains aspartic acid 87 residue replaced with a glycine residue or valine 92 residue replaced with an alanine residue or a combination or conservative equivalent thereof. In yet some other embodiments, the soluble AXL variant polypeptide contains an alanine residue replaced with a valine residue. In yet some other embodiments, the soluble AXL variant polypeptide contains glycine 32 residue replaced with a serine residue, aspartic acid 87 residue replaced with a glycine residue, valine 92 residue replaced with an alanine residue, glycine 127 residue replaced with an arginine residue or alanine 72 residue replaced with a valine residue or a combination or conservative equivalent thereof. In still some other embodiments, the soluble AXL variant polypeptide comprises amino acid changes relative to the wild-type AXL sequence (SEQ ID NO: 1) at the following positions: (a) glutamic acid 26; (b) valine 79; (c) valine 92; and (d) glycine 127. In still some other embodiments, the soluble AXL variant polypeptide contains glutamic acid 26 residue replaced with a glycine residue, valine 79 residue replaced with a methionine residue, valine 92 residue replaced with an alanine residue, or glycine 127 residue replaced with a glutamic acid residue or a combination or conversative equivalent thereof.

In still yet some other embodiments, the soluble AXL variant polypeptide comprises at least amino acids 1-437, 19-437, 130-437, 19-132, 1-132 of the wild-type AXL polypeptide (SEQ ID NO: 1). In still yet some other embodiments, the soluble AXL variant polypeptide is a fusion protein comprising an Fc domain.

In one embodiment, the soluble AXL variant polypeptide has an affinity of at least about $1\times10^{-5}$ M for GAS6. In another embodiment, the soluble AXL variant polypeptide has an affinity of at least about $1\times10^{-6}$ M, for GAS6. In yet another embodiment, the soluble AXL variant polypeptide has an affinity of at least about $1\times10^{-7}$ M for GAS6. In yet another embodiment, the soluble AXL variant polypeptide has an affinity of at least about $1\times10^{-8}$ M for GAS6. In yet another embodiment, the soluble AXL variant polypeptide has an affinity of at least about $1\times10^{-9}$ M, $1\times10^{-10}$M, $1\times10^{-11}$M, or $1\times10^{-12}$M for GAS6. In various embodiments described herein, the soluble AXL variant polypeptide exhibits an affinity to GAS6 that is at least about 2-fold stronger than the affinity of the wild-type AXL polypeptide. In some embodiments, the soluble AXL variant polypeptide exhibits an affinity to GAS6 that is at least about 3-fold, 4-fold, 5-fold, 10-fold, 15-fold, 20-fold, 25-fold, or 30-fold stronger than the affinity of the wild-type AXL polypeptide.

In another embodiment, the present invention provides isolated antibodies or fragments thereof which specifically bind to a GAS6 protein (SEQ ID NO: 2). In some embodiments, the isolated antibody or fragment thereof is a monoclonal antibody, a humanized antibody, a chimeric antibody, a single chain antibody (ScFv), or a combination thereof. In some other embodiments, the isolated antibody or fragment thereof binds an epitope comprised in one or more amino acid regions of GAS6 selected from the group consisting of R299-T317, V364-P372, R389-N396, D398-A406, E413-H429, and W450-M468. In yet some other embodiments, the isolated antibody or fragment thereof binds an epitope comprised in the amino acid region selected from the group consisting of RMFSGTPVIRLRFKRLQPT (SEQ ID NO: 3), VGRVTSSGP (SEQ ID NO: 4), RNLVIKVN (SEQ ID NO: 5), DAVMKIAVA (SEQ ID NO: 6), ERGLYHLNLTVG-GIPFH (SEQ ID NO: 7), and WLNGEDTTIQETVKVN-TRM (SEQ ID NO: 8).

In yet another embodiment, the present invention provides methods of treating, reducing, or preventing the metastasis or invasion of a tumor in a mammalian patient. In one embodiment, the method comprises administering to said patient an effective dose of a soluble AXL variant polypeptide or an isolated anti-GAS6 antibody or fragment thereof.

In still another embodiment, the present invention provides methods of treating, reducing, or preventing the metastasis or invasion of a tumor in a mammalian patient. In one embodiment, the method comprises administering one or more inhibitors selected from the group consisting of (a) an inhibitor of AXL activity (b) an inhibitor of GAS6 activity; and (c) an inhibitor of AXL-GAS6 interaction. In various embodiments described herein, the inhibitor is a polypeptide, a polynucleotide, a small molecule, an antibody, an antibody fragment, or antibody drug-conjugate.

In still yet another embodiment, the present invention provides methods of determining the ability of a tumor to undergo invasion or metastasis in a subject. In one embodiment, the method comprises detecting the level of AXL activity and/or GAS6 activity in a biological sample from a subject with a tumor; and comparing the level of the AXL and/or GAS6 activity in the biological sample to predetermined level, wherein an increase over the predetermined level is indicative of a predisposition of the tumor to invasion or metastasize.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 18. Raw Data of Metastatic Burden as Determined by ex vivo Bioluminescence Imaging 4T1 mouse breast cancer xenograft model.

FIG. 19. Raw Data of Metastatic Burden as Determined by qPCR 4T1 mouse breast cancer xenograft model.

DEFINITIONS

Figure 1:
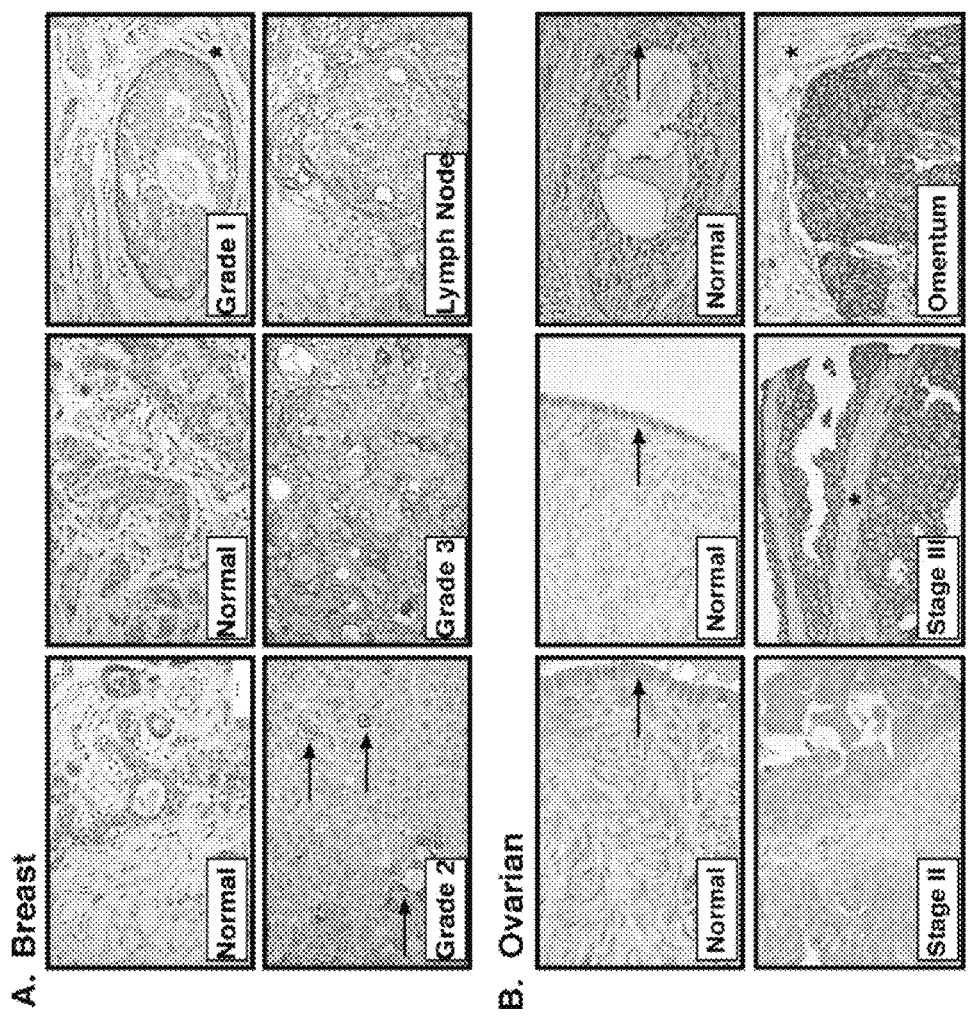
FIG. 1. AXL expression correlates tumor progression and metastasis in human breast and ovarian cancer. A. Representative images of AXL immunohistochemical staining in normal breast tissue (normal), primary infiltrating ductal carcinoma (grade 1,2, and 3) and lymph node metastases (lymph node). Note that high levels of membranous AXL staining were present a grade 2 (arrows), grade 3, and lymph node metastases. No AXL staining was observed in normal or tumor stroma (*). B. Representative images of AXL immunohistochemical staining in normal ovarian epithelium (arrow), stage II, stage III, and omentum metastasis derived from patients with serous adenocarcinoma. Note that normal and tumor stroma were negative for AXL staining (*).

In the description that follows, a number of terms conventionally used in the field of cell culture are utilized extensively. In order to provide a clear and consistent understanding of the specification and claims, and the scope to be given to such terms, the following definitions are provided.

"Inhibitors," "activators," and "modulators" of AXL on metastatic cells or its ligand GAS6 are used to refer to inhibitory, activating, or modulating molecules, respectively, identified using in vitro and in vivo assays for receptor or ligand binding or signaling, e.g., ligands, receptors, agonists, antagonists, and their homologs and mimetics.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. All single letters used in the present invention to represent amino acids are used according to recognized amino acid symbols routinely used in the field, e.g., A means Alanine, C means Cysteine, etc. An amino acid is represented by a single letter before and after the relevant position to reflect the change from original amino acid (before the position) to changed amino acid (after position). For example, A19T means that amino acid alanine at position 19 is changed to threonine.

The terms "subject," "individual," and "patient" are used interchangeably herein to refer to a mammal being assessed for treatment and/or being treated. In an embodiment, the mammal is a human. The terms "subject," "individual," and "patient" thus encompass individuals having cancer, including without limitation, adenocarcinoma of the ovary or prostate, breast cancer, glioblastoma, etc., including those who have undergone or are candidates for resection (surgery) to remove cancerous tissue. Subjects may be human, but also include other mammals, particularly those mammals useful as laboratory models for human disease, e.g. mouse, rat, etc.

The term "tumor," as used herein, refers to all neoplastic cell growth and proliferation, whether malignant or benign, and all pre-cancerous and cancerous cells and tissues.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. In general, cells of interest for detection, analysis, classification, or treatment in the present application include precancerous (e.g., benign), malignant, pre-metastatic, metastatic, and non-metastatic cells. Examples of cancer include but are not limited to, ovarian cancer, glioblastoma, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body. Therefore, the present invention contemplates a method of determining the risk of further growth of one or more cancerous tumors in an organ or body part which is not directly connected to the organ of the original cancerous tumor and/or any steps in a process leading up to that growth.

Depending on the nature of the cancer, an appropriate patient sample is obtained. As used herein, the phrase "cancerous tissue sample" refers to any cells obtained from a cancerous tumor. In the case of solid tumors which have not metastasized, a tissue sample from the surgically removed tumor will typically be obtained and prepared for testing by conventional techniques.

The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure (e.g., radiation, a surgical procedure, etc.), for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of any metastatic tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. In tumor (e.g., cancer) treatment, a therapeutic agent may directly decrease the metastasis of tumor cells.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with neoplasia, e.g., tumor or cancer. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

According to the present invention, the first therapeutic can be any suitable therapeutic agent, e.g., cytotoxic agents. One exemplary class of cytotoxic agents are chemotherapeutic agents, e.g., they can be combined with treatment to inhibit AXL or GAS6 signaling. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate. For ovarian cancer treatment, a preferred chemotherapeutic agent with which an AXL or GAS6 signaling inhibitor can be combined is paclitaxel (Taxol™).

Other combination therapies are radiation, surgery, and hormone deprivation (Kwon et al., Proc. Natl. Acad. Sci U.S.A., 96: 15074-9, 1999). Angiogenesis inhibitors can also be combined with the methods of the invention.

"Concomitant administration" of a known cancer therapeutic drug with a pharmaceutical composition of the present invention means administration of the drug and AXL inhibitor at such time that both the known drug and the composition of the present invention will have a therapeutic effect. Such concomitant administration may involve concurrent (i.e. at the same time), prior, or subsequent administration of the drug with respect to the administration of a compound of the present invention. A person of ordinary skill in the art would have no difficulty determining the appropriate timing, sequence and dosages of administration for particular drugs and compositions of the present invention.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound (s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

DETAILED DESCRIPTIONS

According to the present invention, it provides soluble AXL variants, e.g., soluble AXL variant polypeptides that have a binding activity to GAS6 that is substantially equal to or better than the binding activity of a wild-type AXL polypeptide. In some embodiments of the invention, the soluble AXL variant polypeptides are utilized as therapeutic agents.

The AXL protein, with reference to the native sequence of SEQ ID NO: 1, comprises an immunoglobulin (Ig)-like domain from residues 27-128, a second Ig-like domain from residues 139-222, fibronectin type 3 domains from residues 225-332 and 333-427, intracellular domain from residues 473-894 including tyrosine kinase domain. The tyrosine residues at 779, 821 and 866 become autophosphorylated upon receptor dimerization and serve as docking sites for intracellular signaling molecules. The native cleavage site to release the soluble form of the polypeptide lies at residues 437-451.

For the purposes of the invention, a soluble form of AXL is the portion of the polypeptide that is sufficient to bind GAS6 at a recognizable affinity, e.g., high affinity, which normally lies between the signal sequence and the transmembrane domain, i.e. generally from about SEQ ID NO: 1 residue 19-437, but which may comprise or consist essentially of a truncated version of from about residue 19, 25, 30, 35, 40, 45, 50 to about residue 132, 450, 440, 430, 420, 410, 400, 375, 350, to 321, e.g., residue 19-132. In some embodiments, a soluble form of AXL lacks the transmembrane domain, and optionally the intracellular domain.

Soluble AXL variant polypeptides (sAXL variants) of the present invention include one or more amino acid modifications within the soluble form of wild-type AXL, e.g., one or more amino acid modifications that increase its affinity for GAS6. According to the present invention, amino acid modifications include any naturally occurring or man-made amino acid modifications known or later discovered in the field. In some embodiments, amino acid modifications include any naturally occurring mutation, e.g., substitution, deletion, addition, insertion, etc. In some other embodiments, amino acid modifications include replacing existing amino acid with another amino acid, e.g., a conservative equivalent thereof. In yet some other embodiments, amino acid modifications include replacing one or more existing amino acids with non-natural amino acids or inserting one or more non-natural amino acids. In still some other embodiments, amino acid modifications include at least 1, 2, 3, 4, 5, or 6 or 10 amino acid mutations or changes.

In some exemplary embodiments, one or more amino acid modifications can be used to alter properties of the soluble form of AXL, e.g., affecting the stability, binding activity and/or specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

In some embodiments, sAXL variants of the present invention include one or more amino acid modifications within one or more regions of residue 18 to 130, residue 10 to 135, residue 15 to 45, residue 60 to 65, residue 70 to 80, residue 85 to 90, residue 91 to 99, residue 104 to 110, residue 111 to 120, residue 125 to 130, residue 19 to 437, residue 130 to 437, residue 19 to 132, residue 21 to 132, residue 21 to 121, residue 26 to 132, or residue 26 to 121 of wild-type AXL (SEQ ID NO: 1). In some other embodiments, sAXL variants of the present invention include one or more amino acid modifications within one or more regions of residue 20 to 130, residue 37 to 124 or residue 141 to 212 of wild-type AXL (SEQ ID NO: 1). In yet some other embodiments, sAXL variants of the present invention include one or more amino acid modifications at one or more positions of position 19, 23, 26, 27, 32, 33, 38, 44, 61, 65, 72, 74, 78, 79, 86, 87, 88, 90, 92, 97, 98, 105, 109, 112, 113, 116, 118, 127, or 129 of wild-type AXL (SEQ ID NO: 1).

In yet some other embodiments, sAXL variants of the present invention include one or more amino acid modifications including without any limitation 1) A19T, 2) T23M, 3) E26G, 4) E27G or E27K, 5) G32S, 6) N33S, 7) T38I, 8) T44A, 9) H61Y, 10) D65N, 11) A72V, 12) S74N, 13) Q78E, 14) V79M, 15) Q86R, 16) D87G, 17) D88N, 18) I90M or I90V, 19) V92A, V92G or V92D, 20) I97R, 21) T98A or T98P, 22) T105M, 23) Q109R, 24) V112A, 25) F113L, 26) H116R, 27) T118A, 28) G127R or G127E, and 29) E129K and a combination thereof.

In yet some other embodiments, sAXL variants of the present invention include one or more amino acid modifications at position 32, 87, 92, or 127 of wild-type AXL (SEQ ID NO: 1) or a combination thereof, e.g., G32S; D87G; V92A and/or G127R. In yet some other embodiments, sAXL variants of the present invention include one or more amino acid modifications at position 26, 79, 92, 127 of wild-type AXL (SEQ ID NO: 1) or a combination thereof, e.g., E26G, V79M; V92A and/or G127E. In yet some other embodiments, sAXL variants of the present invention include one or more amino acid modifications at position 32, 87, 92, 127 and/or 72 of wild-type AXL (SEQ ID NO: 1) or a combination thereof, e.g., G32S; D87G; V92A; G127R and/or A72V. In yet some other embodiments, sAXL variants of the present invention include one or more amino acid modifications at position 87, 92 and/or 127 of wild-type AXL (SEQ ID NO: 1) or a combination thereof, e.g., D87G; V92A; and/or G127R. In yet some other embodiments, sAXL variants of the present invention include one or more amino acid modifications at position 32, 92, and/or 127 of wild-type AXL (SEQ ID NO: 1)

or a combination thereof, e.g., G32S; V92A; and/or G127R. In yet some other embodiments, sAXL variants of the present invention include one or more amino acid modifications at position 32, 87 and/or 127 of wild-type AXL (SEQ ID NO: 1) or a combination thereof, e.g., G32S; D87G; and/or G127R. In yet some other embodiments, sAXL variants of the present invention include one or more amino acid modifications at position 32, 87 and/or 92 of wild-type AXL (SEQ ID NO: 1) or a combination thereof, e.g., G32S; D87G; and/or V92A. In yet some other embodiments, sAXL variants of the present invention include one or more amino acid modifications at position 26, 79, 92, 127 of wild-type AXL (SEQ ID NO: 1) or a combination thereof, e.g., E26G, V79M; V92A and/or G127E. In yet some other embodiments, sAXL variants of the present invention include one or more amino acid modifications at position 87 and 92 of wild-type AXL (SEQ ID NO: 1) or a combination thereof, e.g., D87G and V92A. In yet some other embodiments, sAXL variants of the present invention include at least one amino acid modification at position 72 of wild-type AXL (SEQ ID NO: 1), e.g., A72V.

According to the present invention, sAXL variants of the present invention can be further modified, e.g., joined to a wide variety of other oligopeptides or proteins for a variety of purposes. For instance, various post-translation or post-expression modifications can be carried out with respect to sAXL variants of the present invention. For example, by employing the appropriate coding sequences, one may provide farnesylation or prenylation. In some embodiments, the sAXL variants of the present invention can be PEGylated, where the polyethyleneoxy group provides for enhanced lifetime in the blood stream. The sAXL variants of the present invention can also be combined with other proteins, such as the Fc of an IgG isotype, which can be complement binding, with a toxin, such as ricin, abrin, diphtheria toxin, or the like, or with specific binding agents that allow targeting to specific moieties on a target cell.

In some embodiments, sAXL variants of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some other embodiments, the second polypeptide is part or whole of Fc region. In some other embodiments, the second polypeptide is any suitable polypeptide that is substantially similar to Fc, e.g., providing increased size and/or additional binding or interaction with Ig molecules. In yet some other embodiments, the second polypeptide is part or whole of an albumin protein, e.g., a human serum albumin protein. In some embodiments, the second polypeptide is a protein or peptide that binds to albumin.

In some other embodiments, the second polypeptide is useful for handling sAXL variants, e.g., purification of sAXL variants or for increasing its stability in vitro or in vivo. For example, sAXL variants of the present invention can be combined with parts of the constant domain of immunoglobulins (IgG), resulting in chimeric or fusion polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. EPA 394,827; Traunecker et al., Nature, 331: 84-86, 1988. Fusion proteins having disulfide-linked dimeric structures (due to the IgG) can also be more efficient in binding and neutralizing other molecules, than the monomeric secreted protein or protein fragment alone. Fountoulakis et al., J. Biochem. 270: 3958-3964,1995.

In yet some other embodiments, the second polypeptide is a marker sequence, such as a peptide which facilitates purification of the fused polypeptide. For example, the marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., Cell 37: 767, 1984.

In still some other embodiments, the second polypeptide is an entity useful for improving the characteristics of sAXL variants of the present invention. For instance, a region of additional amino acids, particularly charged amino acids, may be added to the N-terminus of the polypeptide to improve stability and persistence during purification from the host cell or subsequent handling and storage. Also, peptide moieties may be added to the sAXL variants of the present invention to facilitate purification and subsequently removed prior to final preparation of the polypeptide. The addition of peptide moieties to facilitate handling of polypeptides are familiar and routine techniques in the art.

In still yet some embodiments, sAXL variants of the present invention has a binding activity to GAS6 that is at least equal or better than the wild-type AXL. In some other embodiments, sAXL variants of the present invention has a binding activity or affinity to GAS6 that is at least 1-fold, 2-fold, 3-fold, 4-fold, 5-fold, or 6-fold greater than that of the wild-type AXL. In some other embodiments, sAXL variants of the present invention has a binding activity or affinity to GAS6 of at least about $1 \times 10^{-6}$, $1 \times 10^{-7}$, $1 \times 10^{-8}$ or $1 \times 10^{-9}$ M $1 \times 10^{-10}$M, m $1 \times 10^{-11}$M or $1 \times 10^{-12}$M. In yet some other embodiments, sAXL variants of the present invention is capable of inhibiting, inhibits or competes with wild-type AXL binding to GAS6 either in vivo, in vitro or both. In yet some other embodiments, sAXL variants of the present invention inhibit or compete with the binding of AXL S6-1, AXL S6-2, and/or AXL S6-5 as provided in Example 2 of the present application. In yet some other embodiments, sAXL variants of the present invention inhibit or compete with the binding of any sAXL variant provided in Example 2 of the present application. In yet some other embodiments, sAXL variants of the present invention inhibit or compete with the binding of AXL S6-1, AXL S6-2, and/or AXL S6-5 as provided in Example 4 of the present application. In yet some other embodiments, sAXL variants of the present invention inhibit or compete with the binding of any sAXL variant provided in Example 4 of the present application. In yet some other embodiments, sAXL variants of the present invention inhibit or compete with the binding of AXL S6-1, AXL S6-2, and/or AXL S6-5 as provided in Example 5 of the present application. In yet some other embodiments, sAXL variants of the present invention inhibit or compete with the binding of any sAXL variant provided in Example 5 of the present application.

The ability of a molecule to bind to GAS6 can be determined, for example, by the ability of the putative ligand to bind to GAS6 coated on an assay plate. In one embodiment, the binding activity of sAXL variants of the present invention to a GAS6 can be assayed by either immobilizing the ligand, e.g., GAS6 or the sAXL variant. For example, the assay can include immobilizing GAS6 fused to a His tag onto Ni-activated NTA resin beads. Agents can be added in an appropriate buffer and the beads incubated for a period of time at a given temperature. After washes to remove unbound material, the bound protein can be released with, for example, SDS, buffers with a high pH, and the like and analyzed.

In still yet other embodiments, sAXL variants of the present invention has a better thermal stability than the thermal stability of a wild-type AXL. In some embodiments, the melting temperature of sAXL variants of the present invention is at least 5° C., 10° C., 15° C., or 20° C. higher than the melting temperature of a wild-type AXL.

According to the present invention, sAXL variants of the present invention can also include one or more modifications that do not alter primary sequences of the sAXL variants of the present invention. For example, such modifications can include chemical derivatization of polypeptides, e.g., acetylation, amidation, carboxylation, etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. In some embodiments, sAXL variants of the present invention include sAXL variant having phosphorylated amino acid residues, e.g. phosphotyrosine, phosphoserine, or phosphothreonine.

In some other embodiments, sAXL variants of the present invention include sAXL variants further modified to improve their resistance to proteolytic degradation or to optimize solubility properties or to render them more suitable as a therapeutic agent. For example, sAXL variants of the present invention further include analogs of a sAXL variant containing residues other than naturally occurring L-amino acids, e.g. D-amino acids or non-naturally occurring synthetic amino acids. D-amino acids may be substituted for some or all of the amino acid residues.

In yet some other embodiments, sAXL variants of the present invention include at least two same or different sAXL variants linked covalently or non-covalently. For example, in some embodiments, sAXL variants of the present invention include two, three, four, five, or six same or different sAXL variants linked covalently, e.g., so that they will have the appropriate size, but avoiding unwanted aggregation.

According to the present invention, sAXL variants of the present invention can be produced by any suitable means known or later discovered in the field, e.g., produced from eukaryotic or prokaryotic cells, synthesized in vitro, etc. Where the protein is produced by prokaryotic cells, it may be further processed by unfolding, e.g. heat denaturation, DTT reduction, etc. and may be further refolded, using methods known in the art.

The polypeptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. Direct chemical synthesis methods include, for example, the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

In some embodiments, the present invention provides expression vectors for in vitro or in vivo expression of one or more sAXL variants of the present invention, either constitutively or under one or more regulatory elements. In some embodiments, the present invention provides a cell population comprising one or more expression vectors for expressing sAXL variants of the present invention, either constitutively or under one or more regulatory elements.

According to another aspect of the invention, it provides isolated antibodies or fragments thereof which specifically binds to a GAS6 protein. GAS6 (growth arrest-specific 6) belongs structurally to the family of plasma vitamin K-dependent proteins. GAS6 has a high structural homology with the natural anticoagulant protein S, sharing the same modular composition and having 40% sequence identity. GAS6 has growth factor-like properties through its interaction with receptor tyrosine kinases of the TAM family; Tyro3, AXL and MerTK. Human GAS6 is a 678 amino acid protein that consists of a gamma-carboxyglutamate (Gla)-rich domain that mediates binding to phospholipid membranes, four epidermal growth factor-like domains, and two laminin G-like (LG) domains. The sequence of the transcript variants of human GAS6 may be accessed at Genbank at NM_001143946.1; NM_001143945.1; and NM_000820.2, respectively.

GAS6 employs a unique mechanism of action, interacting through its vitamin K-dependent GLA (gamma-carboxyglutamic acid) module with phosphatidylserine-containing membranes and through its carboxy-terminal LamG domains with the TAM membrane receptors.

According to the present invention, isolated antibodies of the present invention include any isolated antibodies with a recognizable binding specificity against GAS6. In some embodiments, isolated antibodies are partially or fully humanized antibodies. In some other embodiments, isolated antibodies are monoclonal or polyclonal antibodies. In yet some other embodiments, isolated antibodies are chimeric antibodies, e.g., with consistent regions, variable regions and/or CDR3 or a combination thereof from different sources. In yet some other embodiments, isolated antibodies are a combination of various features described herein.

According to the present invention, fragments of the isolated antibodies of the present invention include a polypeptide containing a region of the antibody (either in the context of an antibody scaffold or a non-antibody scaffold) that is sufficient or necessary for a recognizable specific binding of the polypeptide towards GAS6. In some embodiments, fragments of the isolated antibodies of the present invention include variable light chains, variable heavy chains, one or more CDRs of heavy chains or light chains or combinations thereof, e.g., Fab, Fv, etc. In some embodiments, fragments of the isolated antibodies of the present invention include a polypeptide containing a single chain antibody, e.g., ScFv. In yet some embodiments, fragments of the isolated antibodies of the present invention include variable regions only or variable regions in combination with part of Fc region, e.g., CH1 region. In still some embodiments, fragments of the isolated antibodies of the present invention include minibodies, e.g., VL-VH-CH3 or diabodies.

In some embodiments, isolated antibodies of the present invention bind to an epitope comprised in or presented by one or more amino acid regions that interact with AXL. In some other embodiments, isolated antibodies of the present invention bind to an epitope comprised in or presented by one or more amino acid regions of GAS6, e.g., L295-T317, E356-P372, R389-N396, D398-A406, E413-H429, and W450-M468 of GAS6.

In yet some other embodiments, isolated antibodies of the present invention bind to an epitope comprised in or presented by one or more amino acid regions, e.g., LRMFSGTPVIRLRFKRLQPT (SEQ ID NO: 3), EIVGRVTSSGP (SEQ ID NO: 4), RNLVIKVN (SEQ ID NO: 5), DAVMKIAVA (SEQ ID NO: 6), ERGLYHLNLTVGIPFH (SEQ ID NO: 7), and WLNGEDTTIQETVVNRM (SEQ ID NO: 8).

In yet some other embodiments, isolated antibodies of the present invention bind to an epitope comprised in or presented by at least one, two, three, four, five, or six amino acids in a region of L295-T317, E356-P372, R389-N396, D398-A406, E413-H429, and W450-M468 of GAS6. In yet some other embodiments, isolated antibodies of the present invention bind to an epitope comprised in or presented by at least one, two, three, four, five or six amino acids in a region of LRMFSGTPVIRLRFKRLQPT (SEQ ID NO: 3), EIVGRVTSSGP (SEQ ID NO: 4), RNLVIKVN (SEQ ID NO: 5), DAVMKIAVA (SEQ ID NO: 6), ERGLYHLNLTVGIPFH (SEQ ID NO: 7), and WLNGEDTTIQETVVNRM (SEQ ID NO: 8).

In still some other embodiments, isolated antibodies of the present invention is capable of inhibiting, inhibits or competes with the binding between wild-type AXL or sAXL variants of the present invention and GAS6.

According to the present invention, both sAXL variants and isolated antibodies of the present invention can be provided in pharmaceutical compositions suitable for therapeutic use, e.g., for human treatment. In some embodiments, pharmaceutical compositions of the present invention include one or more therapeutic entities of the present invention, e.g., sAXL variants and/or isolated antibodies against GAS6 or pharmaceutically acceptable salts, esters or solvates thereof or any prodrug thereof. In some other embodiments, pharmaceutical compositions of the present invention include one or more therapeutic entities of the present invention in combination with another cytotoxic agent, e.g., another anti-tumor agent. In yet some other embodiments, pharmaceutical compositions of the present invention include one or more therapeutic entities of the present invention in combination with another pharmaceutically acceptable excipient.

In still some other embodiments, therapeutic entities of the present invention are often administered as pharmaceutical compositions comprising an active therapeutic agent, i.e., and a variety of other pharmaceutically acceptable components. (See Remington's Pharmaceutical Science, 15.sup.th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions of the present invention can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

According to yet another aspect of the invention, it provides methods for treating, reducing or preventing tumor metastasis or tumor invasion by inhibiting the AXL signaling pathway and/or GAS6 signaling pathway. In some embodiments, methods of the present invention include inhibiting the activity of AXL, the activity of GAS6, or the interaction between AXL and GAS6. For example, the activity of AXL or GAS6 can be inhibited at the gene expression level, mRNA processing level, translation level, post-translation level, protein activation level, etc. In some other examples, the activity of AXL or GAS6 can be inhibited by small molecules, biological molecules, e.g., polypeptides, polynucleotides, antibodies, antibody drug conjugates, etc. In some other examples, the activity of AXL or GAS6 can be inhibited by one or more sAXL variants or isolated antibodies of the present invention.

In yet other embodiments, methods of the present invention include administering to a subject in need of treatment a therapeutically effective amount or an effective dose of a therapeutic entity of the present invention, e.g., an inhibitor of AXL activity or GAS6 activity or an inhibitor of interaction between AXL and GAS6. In some embodiments, effective doses of the therapeutic entity of the present invention, e.g. for the treatment of metastatic cancer, described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

In some embodiments, the dosage may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor metastasis or tumor invasion of ovarian cancer, breast cancer, lung cancer, liver cancer, colon cancer, gallbladder cancer, pancreatic cancer, prostate cancer, and/or glioblastoma.

In still yet some other embodiments, for prophylactic applications, pharmaceutical compositions or medicaments are administered to a patient susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

In still yet some other embodiments, for therapeutic applications, therapeutic entities of the present invention are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved. Typically, the response is monitored and repeated dosages are given if there is a recurrence of the cancer.

According to the present invention, compositions for the treatment of metastatic cancer can be administered by parenteral, topical, intravenous, intratumoral, oral, subcutaneous, intraarterial, intracranial, intraperitoneal, intranasal or intramuscular means. The most typical route of administration is intravenous or intratumoral although other routes can be equally effective.

For parenteral administration, compositions of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., Nature 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul et al., *Eur. J. Immunol.* 25: 3521-24, 1995; Cevc et al., Biochem. Biophys. Acta 1368: 201-15, 1998.

The pharmaceutical compositions are generally formulated as sterile, substantially isotonic and in full compliance with all Good Manufacturing Practice (GMP) regulations of the U.S. Food and Drug Administration.

Preferably, a therapeutically effective dose of the antibody compositions described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1).

Also within the scope of the invention are kits comprising the compositions (e.g., soluble AXL variants and formulations thereof) of the invention and instructions for use. The kit can further contain a least one additional reagent. Kits typically include a label indicating the intended use of the contents of the kit. The term label includes any writing, or recorded material supplied on or with the kit, or which otherwise accompanies the kit.

According to yet another aspect of the invention, it provides methods for determining the ability of a tumor to undergo tumor invasion and/or metastasis by detecting and/or determining the level of AXL activity or GAS6 activity in a biological sample from a subject of interest. In some embodiment, the level of AXL activity or GAS6 activity is measured by the level of mRNA expression, the level of protein expression, the level of protein activation or any suitable indicator corresponding to the activity of AXL or GAS6 either directly or indirectly. In some embodiments, the level of AXL activity or GAS6 activity in a biological sample is further compared to a predetermined level, e.g., standard level obtained by establishing normal levels or ranges of AXL activity or GAS6 activity based on a population of samples from tumors that do not develop tumor invasion or tumor metastasis or from normal tissues. For example, an increase of AXL activity or GAS6 activity over the predetermined level or standard level is indicative of a predisposition of the tumor to undergo tumor invasion or tumor metastasis.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, examples will be described to illustrate parts of the invention.

EXPERIMENTAL

Example 1

Therapeutic Blockade of AXL Signaling Inhibits Metastatic Tumor Progression

Demonstration of AXL as a therapeutic target for metastatic disease has been largely unexplored, and more importantly no in vivo correlates of AXL targeting have been demonstrated. We show that AXL is a marker of metastases in human breast and ovarian cancer patients, and that the severity of disease in these patients correlates with the amount of AXL protein in the primary tumor. Most importantly, we show that tumor metastasis can be successfully treated in mice with pre-existing metastasis by the administration of soluble AXL ectodomains. Mechanistically, inhibition of AXL signaling in animals with metastatic disease results in decreased invasion and MMP activity. Our findings demonstrate that inhibition of the AXL signaling cascade in tumor cells through the administration of soluble AXL ectodomains is sufficient to inhibit metastatic tumor progression.

In this study, we test whether AXL is a critical factor for metastasis in human cancer and that therapeutic blockade of AXL signaling may be an effective treatment for metastatic disease. We utilize both genetic and therapeutic approaches to directly assess the role of AXL in the initiation and progression of metastatic breast and ovarian cancer.

AXL is a marker of tumor progression and metastases in human cancer. We first compared AXL expression in normal tissue, primary tumor, and metastases from patients with breast or ovarian cancer. In 100% of normal adjacent breast cancer specimens, mammary epithelial cells showed diffuse cytoplasmic and nuclear staining for AXL that was considered to be background staining given that AXL is a membrane bound receptor (n=27, FIG. 1A). However in primary breast tumors, membranous AXL staining in tumor epithelium was present in 25% (1/4) of grade 1, 76% (10/13) of grade 2, and 100% (18/18) of grade 3 specimens (FIG. 1A and Table 1). Additionally, AXL was expressed in 88% (8/9) of lymph node metastases.

In serous ovarian cancer specimens, AXL expression was first examined in normal ovarian surface epithelium (OSE) since the majority of ovarian tumors are thought to arise from these cells. In ovarian cancer patient samples that retained normal OSE, AXL was expressed in 0% (0/5) of specimens (FIG. 1B). In contrast, membranous AXL staining in primary tumor epithelium, was present in 66% (6/9) of stage 11 and 83% (53/64) of stage III patient samples (FIG. 1B and Table I). In addition, tumor samples from common metastatic sites such as the omentum and peritoneum showed high AXL expression in 75% (24/32) and 90% (27/30) of specimens respectively (FIG. 1B and Table I) These findings demonstrate that AXL expression within primary tumors correlates with metastasis as shown in advanced disease and metastatic tumors. Furthermore, these data demonstrate that metastases derived from human breast and ovarian cancers express high levels of AXL.

Figure 9:
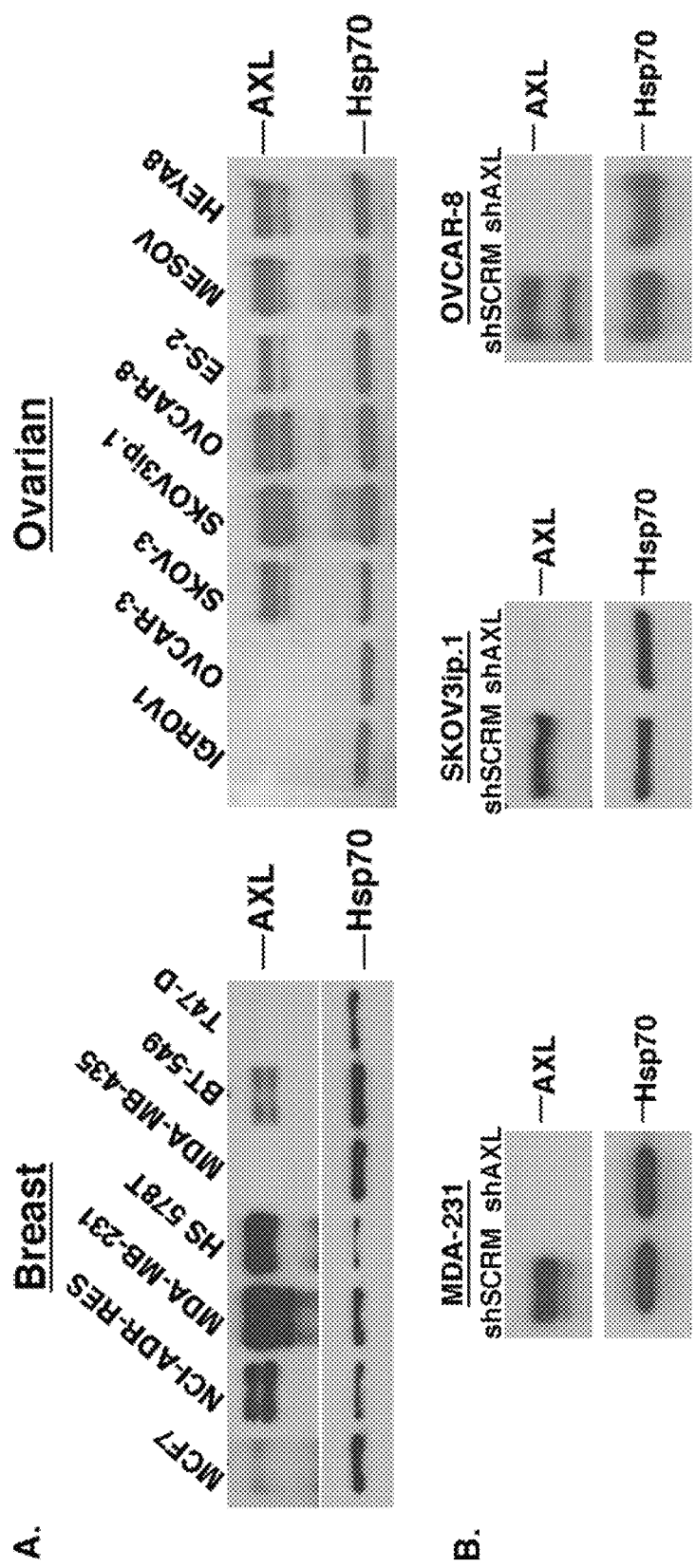
FIG. 9. Generation of AXL deficient breast and ovarian cancer cell lines. A. Western blot analysis of AXL expression in a panel of human breast and ovarian cancer cell lines. Heat shock protein 70 (Hsp70) was used as a protein loading control. B. Western blot analysis of AXL expression in metastatic breast (MDA-231) ovarian (SKOV3ip.1 and OVCAR-8) cancer cell lines stably transfected with shRNA targeting sequences for scramble control (shSCRM) or AXL (shAXL). Note that the shAXL cell lines have a significant reduction in AXL expression.
Figure 10:
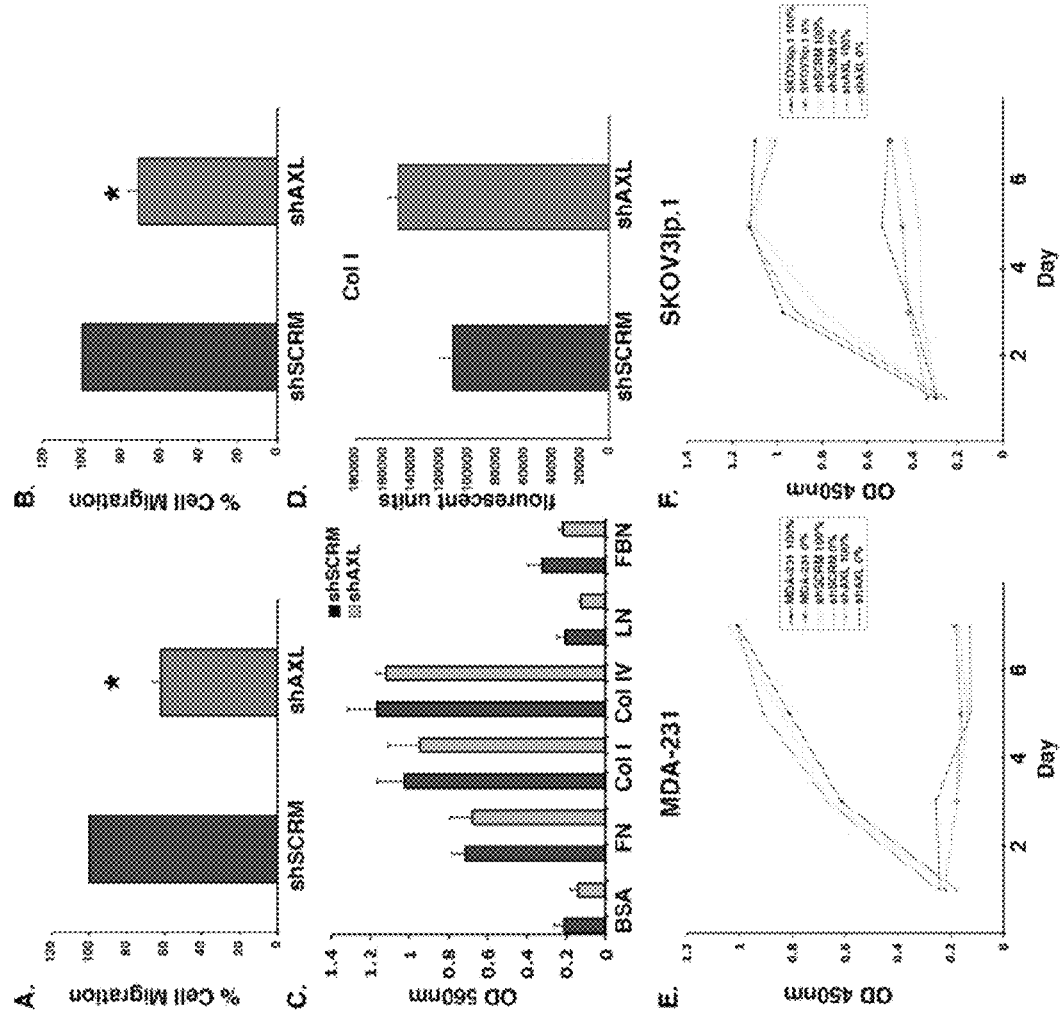
FIG. 10. AXL does not affect breast and ovarian tumor cell adhesion or survival. A-B. Percent cell migration of MDA-231 (A) and SKOV3ip.1 (B) cells in boyden chamber migration assays towards serum as the chemoattractant. C-D. Analysis of MDA-231 (A) SKOV3ip.1 (B) cellular adhesion to extracellular matrix proteins. Abbreviations: bovine serum albumin (BSA), fibronectin (FN), collagen type I (Col I), collagen type IV (Col IV), laminin (LN), fibrinogen (FBN). Error bars represent the standard error of the mean. E-F. Survival analysis of AXL wild-type and AXL deficient MDA-231 (E) and SKOV3ip.1 (F) tumor cells following serum withdrawal as determined by the XTT assay.

AXL is a critical factor for tumor metastasis. To examine the functional role of AXL in metastasis, we utilized a genetic approach to inhibit AXL in mouse models of breast and ovarian metastasis. For this purpose, we screened a panel of human breast and ovarian cancer cell lines for AXL protein expression in order to identify metastatic cell lines with high levels of AXL expression. Similar to our clinical findings, AXL was highly expressed in the majority of metastatic breast (NCI-ADR-RES, MDA-231, HS 578T, 8T-549) and ovarian (SKOV3, OVCAR-8, ES-2, MESOV, HEYA8) cell lines, whereas AXL was expressed at undetectable or low levels in cell lines with low metastatic potential (MCF7, MDA-MB435, T47D, IGROV1, OVCAR-3; FIG. 9). AXL deficient metastatic breast (MDA-231) and ovarian (SKOV3ip.1 and OVCAR-8) cell lines were generated using previously described AXL shRNA targeting sequences. Western blot analysis confirmed that cells expressing shAXL targeting sequences expressed less than 5% of AXL protein compared to cells expressing the scramble control shRNA targeting sequence (shSCRM, FIG. 9B).

Figure 2:
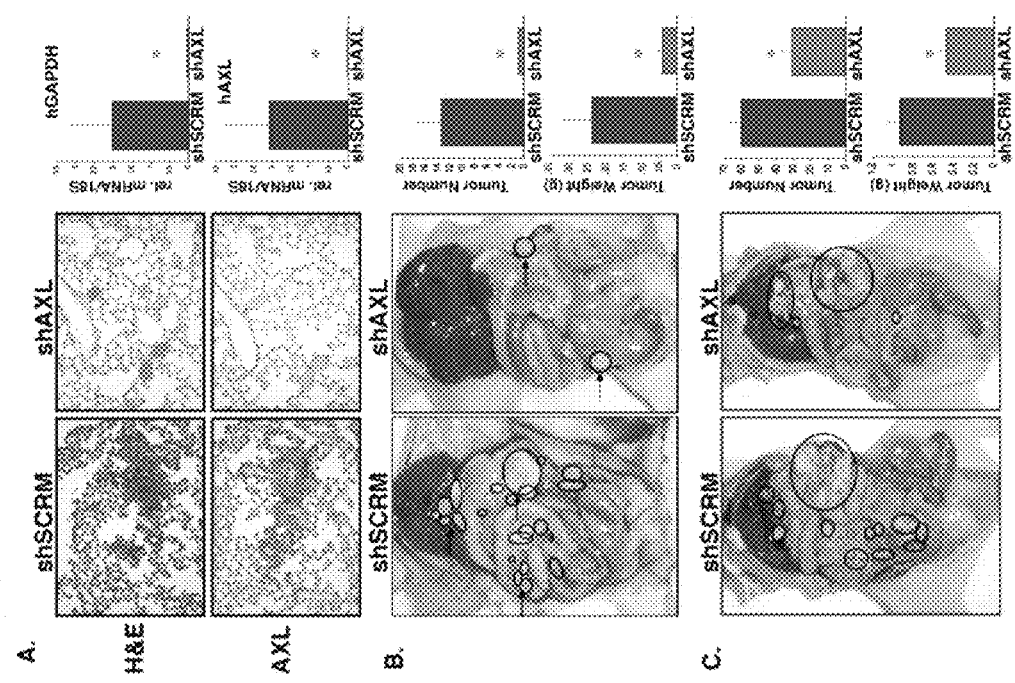
FIG. 2. Genetic inactivation of AXL is sufficient to block breast and ovarian metastasis. A. H&E and AXL immunohistochemical staining in the lungs of mice tail vein injected with shscramble (shSCRM) and shAXL (shAXL) MDA-231 cells. Photographs are representative of 5 mice per group. Graphs depict real time PCR analysis of human GASPDH and AXL expression in whole lung from mice injected with shSCRM or shAXL MDA-231 cells (n=5) B. Photographs of mice taken 28 days after injection with shscramble (shSCRM) and shAXL (shAXL) SKOV3ip.1 cells. Note that the shSCRM injected mice developed numerous metastases in throughout the abdominal cavity (circled). For the shAXL group, the mouse with the greatest tumor burden is shown. Graphs to the right depict the average number of peritoneal metastases per mouse >5 mm in size and the average weight of the largest tumor. Photographs are representative of 5 mice per group. C. Photographs of mice taken 34 days after injection with shSCRM and shAXL OVCAR-8 cells. Note that the shSCRM injected mice developed numerous metastases in throughout the abdominal cavity (circled). Graphs to the right depict the average total number of peritoneal metastases per mouse and the average total tumor weight. Photographs are representative of 8 mice per group.

To directly assess the role of AXL in the late stages of breast tumor metastasis, we injected AXL-wildtype (shSCRM) and AXL-deficient (shAXL) MDA-231 cells into the tail vein of nude mice and evaluated tumor burden in the lungs at day twenty-eight. Microscopic evaluation of lungs revealed that 5/5 mice injected with shRNA scramble (shSCRM) MDA-231 cells developed metastatic foci that stained positive for AXL (FIG. 2A). In contrast, 0/5 mice injected shRNA AXL (shAXL) developed lung metastases upon histologic evaluation (FIG. 2A). In order to quantify tumor burden in the lungs of these mice, we performed real time PCR analysis for human GAPDH. FIG. 2A demonstrates that the lungs of mice injected with shSCRM MDA-231 cells expressed high levels of human GAPDH indicating the presence of metastatic lesions derived from MDA-231 cells. In addition, shSCRM injected mice expressed human AXL in the lung suggesting the presence of AXL positive tumor cells (FIG. 2A). In contrast, mice injected with shAXL tumor cells did not express human GAPDH or AXL in the lung. These findings demonstrate that genetic inactivation of AXL is sufficient to completely suppress the formation of lung metastasis in this model.

To determine whether genetic inactivation of AXL affects the ability of ovarian cancer cells to metastasize in vivo, we compared the ability of shSCRM and shAXL SKOV3ip.1 cells to form metastases using a peritoneal xenograft model of ovarian cancer. This model recapitulates the peritoneal dissemination of human ovarian metastases in which mice develop rapidly progressive disease consisting of ascites and more than 100 small metastatic lesions attached to the mesentery, diaphragm, liver, and other peritoneal surfaces following peritoneal injection of SKOV3ip.1 cells (FIG. 3B). Immunohistochemical analysis of AXL expression in SKOV3ip.1 peritoneal metastases revealed that similar to human ovarian metastases, AXL is highly expressed in SKOV3ip.1 metastatic lesions, indicating that this is a relevant model system to investigate the role of AXL in ovarian metastasis (data not shown). Twenty-eight days following peritoneal injection of shSCRM and shAXL cells, shSCRM mice displayed signs of severe ascites and morbidity necessitating us to sacrifice the mice and investigate changes in tumor burden between the shSCRM and shAXL injected mice. While mice injected with shSCRM cells developed ascites and >100 peritoneal metastases, mice injected with shAXL cells developed very few metastases (FIG. 2B). The average number of peritoneal metastases greater than 5 mm in size was significantly reduced from 13.4+/−4.3 in shSCRM injected mice to 0.8+/−0.5 in shAXL injected mice (FIG. 2B). Similarly, the average weight of these tumors was significantly reduced from 236+/−74 mg in shSCRM-injected mice to 39.2+/−18 mg in shAXL-injected mice (FIG. 2B). In support of these findings, knockdown of AXL expression in OVCAR-8 cells significantly inhibited total ovarian peritoneal tumor mass and tumor number (FIG. 2C). Collectively, these findings demonstrate that AXL is a critical factor for breast and ovarian tumor metastasis.

Figure 3:
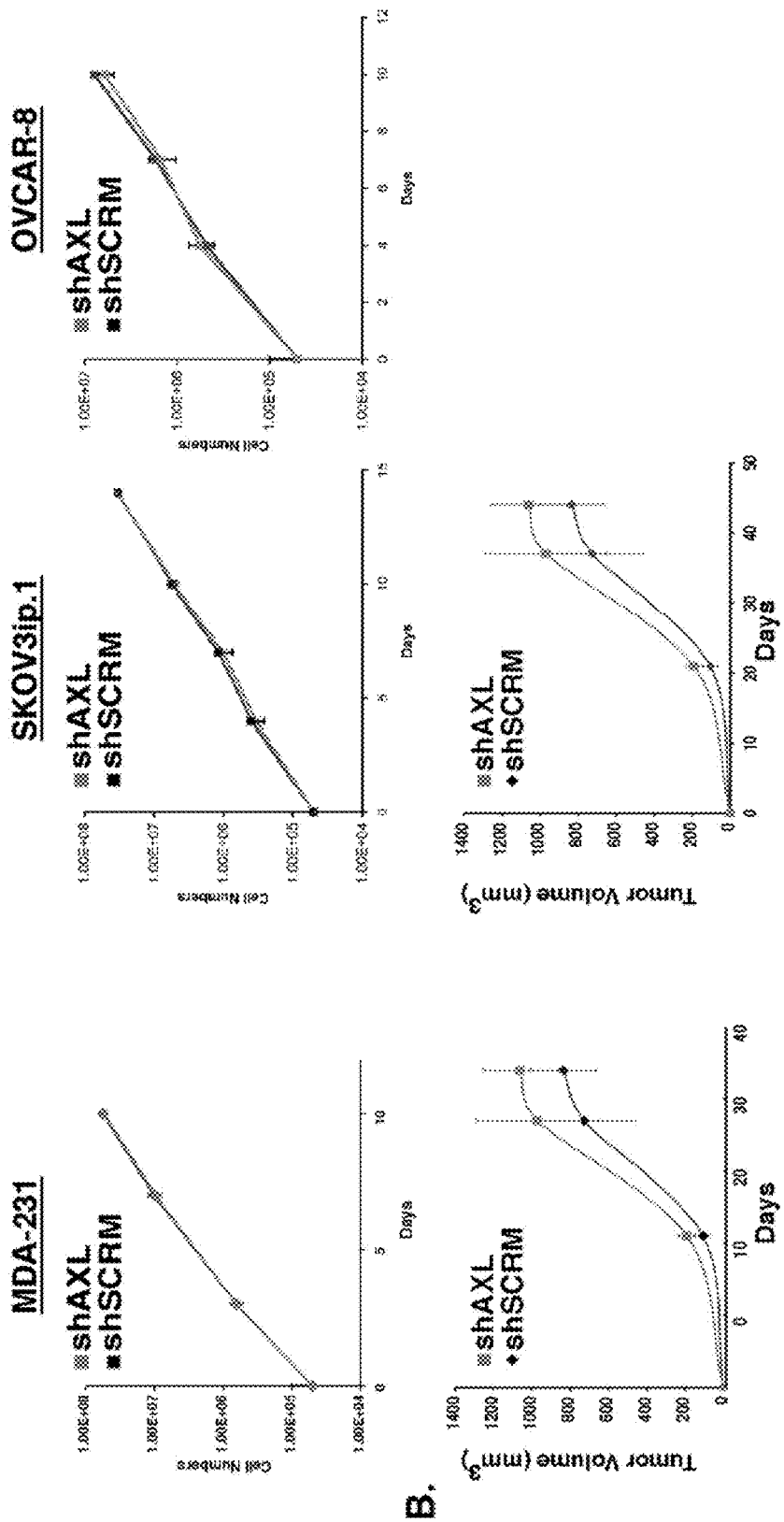
FIG. 3. Genetic inactivation of AXL does not affect breast or ovarian tumor cell proliferation in vitro or growth in vivo. A. Cellular growth curves for MDA-231, SKOV3ip.1, and OVCAR-8 cells stably expressing shRNA targeting sequences for scramble control (shSCRM) or AXL (shAXL). Measurements were performed in triplicate and error bars represent the S.E.M. B. Average tumor volumes of orthotopic MDA-231 (n=8 mice per group) and subcutaneous SKOV3ip.1 tumors (n=4 mice per group) grown over a 48-day time course. Error bars represent the S.E.M.

Given the important role of AXL in the formation metastasis in vivo, we next sought to determine if AXL specifically regulates metastasis, or if AXL plays a general role in the regulation of tumor cell proliferation and growth. To address these questions, we performed in vitro proliferation assays in which total cell numbers between AXL wild type (shSCRM) and AXL deficient (shAXL) cells were counted over a 10-14 day period. We found no significant difference in cellular growth curves between shSCRM and shAXL MDA-231, SKOV3ip.1 or OVCAR-8 cells (FIG. 3). Similarly, no significant difference was observed orthotopic MDA-231 or subcutaneous SKOV3ip.1 tumor growth between shSCRM and shAXL cells (FIG. 3). These findings indicate that AXL is not required tumor cell proliferation or subcutaneous growth in vivo. Overall, our findings indicate that AXL specifically regulates tumor metastasis in breast and ovarian tumors.

Figure 4:
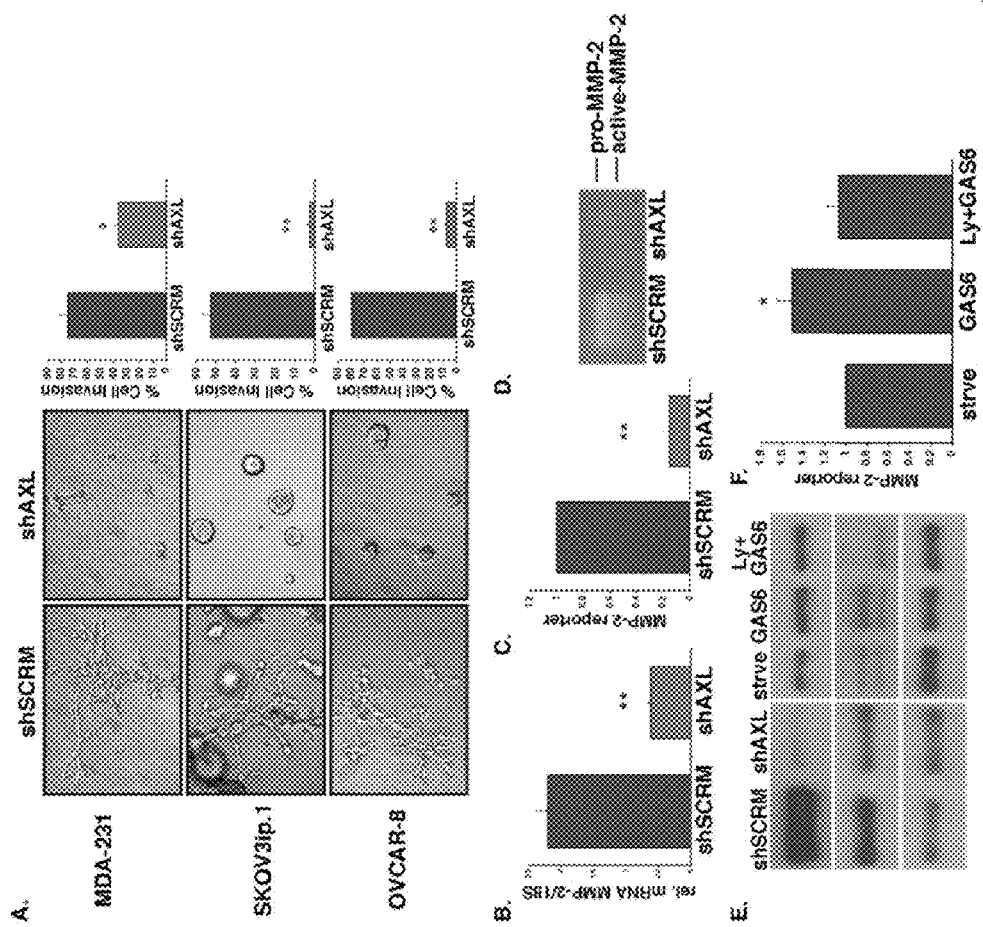
FIG. 4. AXL regulates ovarian and breast tumor cell invasion in vitro. A. Collagen invasion assay of control (shSCRM) and AXL deficient (shAXL) MDA-231, SKOV3ip.1, and OVCAR-8 cells. Photographs are representative of 3 samples per group and were taken 7 days after plating cells in collagen. Note the invasive phenotype observed in AXL wild-type cells (branching) compared to AXL deficient cells (rounded). Graphs show quantification of collagen invasion assays. B. Real time PCR analysis of MMP-2 expression in shAXL and shSCRM SKOV3ip.1 cells. Expression values were normalized to 18S; n=3. Error bars represent the S.E.M. Asterisks indicate a significant increase or decrease in expression compared to shSCRM as determined by the student's t-test (**, P<0.001). C. MMP-2 reporter assay of shSCRM or shAXL SKOV3ip.1 cells (n=6). D. Gelatin zymography assay for pro- and active-MMP2 activity in conditioned media collected from serum starved SKOV3ip.1 cells. E. Western blot analysis of phospho-AKT at Ser473 (P-AKT), total AKT (AKT), and AXL expression in SKOV3ip.1 cells expressing shRNA sequences targeting scramble control (shSCRM) or AXL (shAXL) and starved SKOV3ip.1 cells (strve) treated with GAS6 or the PI3K inhibitor Ly294002 (Ly) with GAS6. F. MMP-2 reporter assay in starved SKOV3ip.1 cells (strve) treated with GAS6 or GAS6 with the PI3K inhibitor Ly294002 (Ly+GAS6).

AXL regulates tumor cell invasion. To determine a potential mechanism for AXL-mediated metastasis, we took an unbiased approach and directly compared the role of AXL in the critical cellular functions associated with the metastatic cascade including proliferation, invasion, migration, adhesion, and survival}. We found that shAXL MDA-231, SKOV3ip.1, and OVCAR-8 cells were significantly impaired in the ability to invade through type I collagen (FIG. 4A). We also observed a modest decrease in cellular migration in shAXL cells, yet we were unable to find a difference in adhesion to ECM proteins or survival following serum withdrawal indicating that AXL predominately affects invasion in the metastatic cascade.

At the molecular level, MMP-9 has recently been identified as an effecter of AXL-mediated invasion in breast cancer cells. Therefore, we investigated whether MMP-9 expression or activity was also altered in AXL-deficient ovarian tumor cells. While SKOV3ip.1 cells do not express MMP-9, we found that MMP-2 was highly expressed in these cells and MMP-2 mRNA was significantly decreased in shAXL cells (FIG. 4B). MMP-2 luciferase reporter assays revealed that MMP-2 promoter activity was significantly decreased in shAXL cells compared to shSCRM cells indicating that AXL regulates MMP-2 at the transcriptional level (FIG. 4C). Gelatin zymography assays indicated that MMP-2 secreted protein levels were also significantly reduced in shAXL cells compared to shSCRM SKOV3ip.1 cells (FIG. 4D). Collectively, these findings suggest a role for AXL as an upstream regulator of MMP-2 expression and activity in human ovarian cancer cells.

We next sought to elucidate the signaling pathways involved in AXL-mediated MMP-2 expression. Activation of AXL by GAS6 has been reported to directly induce a number of intracellular signaling pathways including PI3K, RAS, MAPK, SRC, and PLC. Among these pathways, the PI3K signaling pathway has been shown to regulate MMP-2 expression and invasion in ovarian cancer cells. To determine whether PI3K signaling is affected by loss of AXL in SKOV3ip.1 cells, we performed western blot analysis for phospho-AKT at Ser473 (P-AKT) in AXL-wild type and AXL-deficient SKOV3ip.1 cells. We found a profound inhibition of P-AKT expression in shAXL cells compared to shSCRM SKOV3ip.1 cells (FIG. 4E). Additionally, GAS6 stimulation of starved SKOV3ip.1 cells resulted in a PI3K-dependent induction of P-AKT as treatment with the PI3K inhibitor Ly294002 completely abrogated GAS6-induced P-AKT expression (FIG. 4E). To determine whether the PI3K pathway was involved in AXL-mediated MMP-2 expression, we performed MMP-2 luciferase reporter assays in the presence of GAS6 and Ly294002. The induction of MMP-2 promoter activity following GAS6 stimulation was completely blocked by Ly294002 treatment suggesting that GAS6/AXL signaling regulates MMP-2 expression through the PI3K signaling events (FIG. 4F).

Figure 5:
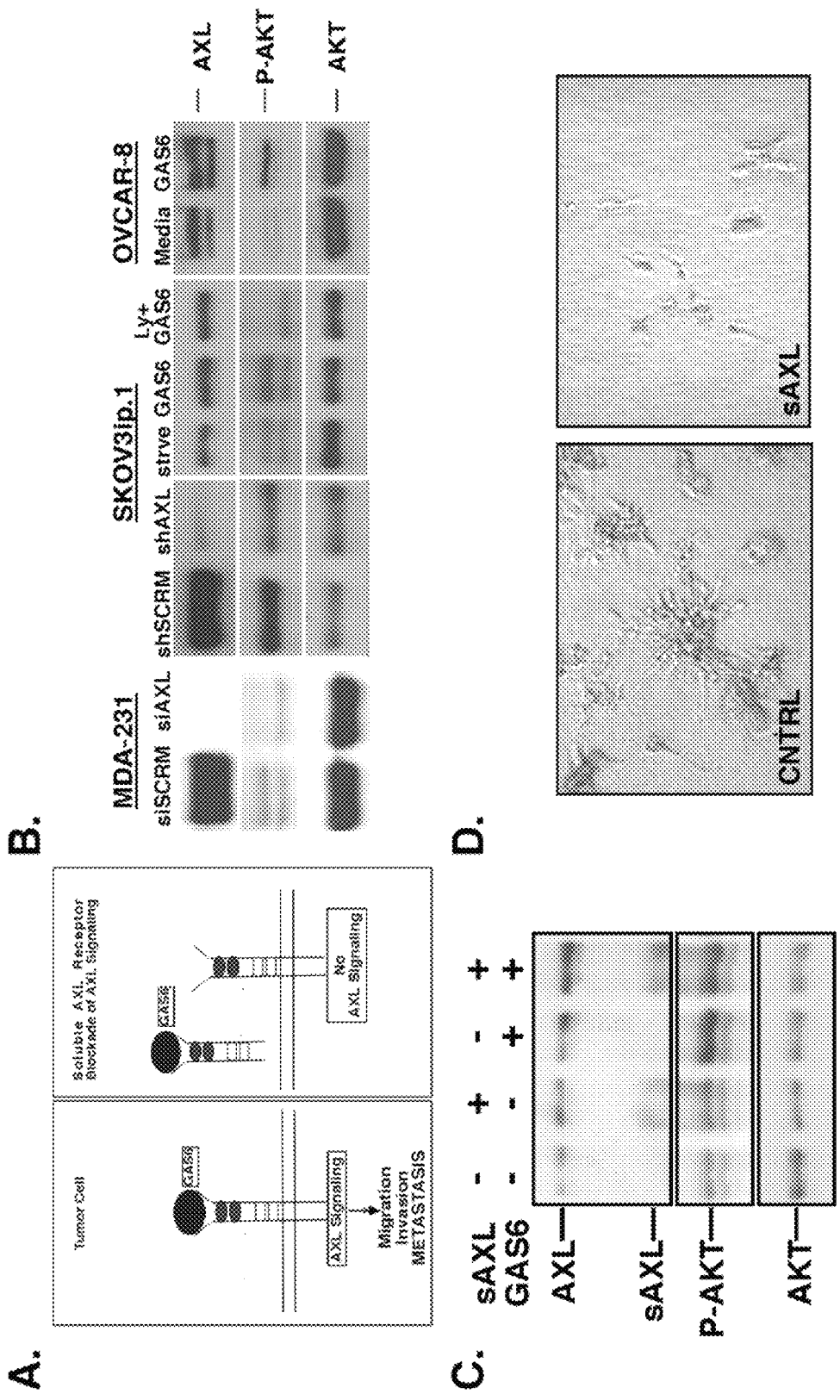
FIG. 5. Soluble AXL ectodomain therapy inhibits AXL signaling and invasion in vitro. A. Schematic representation of the mechanism for soluble AXL therapy. Soluble AXL (sAXL) functions as a decoy receptor to inhibit endogenous AXL signaling. B. Western blot analysis of phospho-AKT at Ser473 (P-AKT), total AKT (AKT), and AXL expression in MDA231, SKOV3ip.1, and OVCAR-8 cells expressing shRNA sequences targeting scramble control (shSCRM) or AXL (shAXL) and starved SKOV3ip.1 cells (strve) treated with GAS6 or the PI3K inhibitor Ly294002 (Ly) with GAS6. C. Western blot analysis of phospho-AKT Ser473 expression in cells treated with conditioned media containing the soluble AXL receptor (sAXL) or control media (−). All cells were starved for 48 hours and treated with GAS6 (+) or vehicle (−). D. Collagen invasion assay in MDA-231 cells treated with conditioned media containing control vector or sAXL.

Therapeutic inhibition of AXL significantly suppresses metastatic tumor progression in mice. Our findings thus far demonstrate that AXL is a critical factor for metastasis and support the hypothesis that therapeutic blockade may be an effective treatment for metastatic disease. To test this hypothesis, we utilized the soluble AXL ectodomain as a therapeutic strategy to inhibit AXL signaling. The soluble AXL ectodomain functionally acts as a decoy receptor and has previously been shown to bind GAS6 with nanomolar affinity in vitro and in vivo (FIG. 5A). We first examined whether treatment with soluble AXL ectodomains is sufficient to inhibit AXL signaling and invasion in metastatic tumor cells. PI3K/AKT signaling is regulated by AXL in a variety of cell types. We found that PI3K/AKT signaling is regulated by GAS6/AXL signaling in SKOV3ip.1 cells and treatment with soluble AXL ectodomains (sAXL) was able to reduce PI3K/AKT activation in GAS6 treated SKOV3ip.1 cells (FIGS. 5B and C). Similarly, treatment of MDA-231 cells in collagen with sAXL was sufficient to dramatically reduce cellular invasion demonstrating that sAXL treatment affects AXL signaling and invasion in vitro (FIG. 5D).

Figure 6:
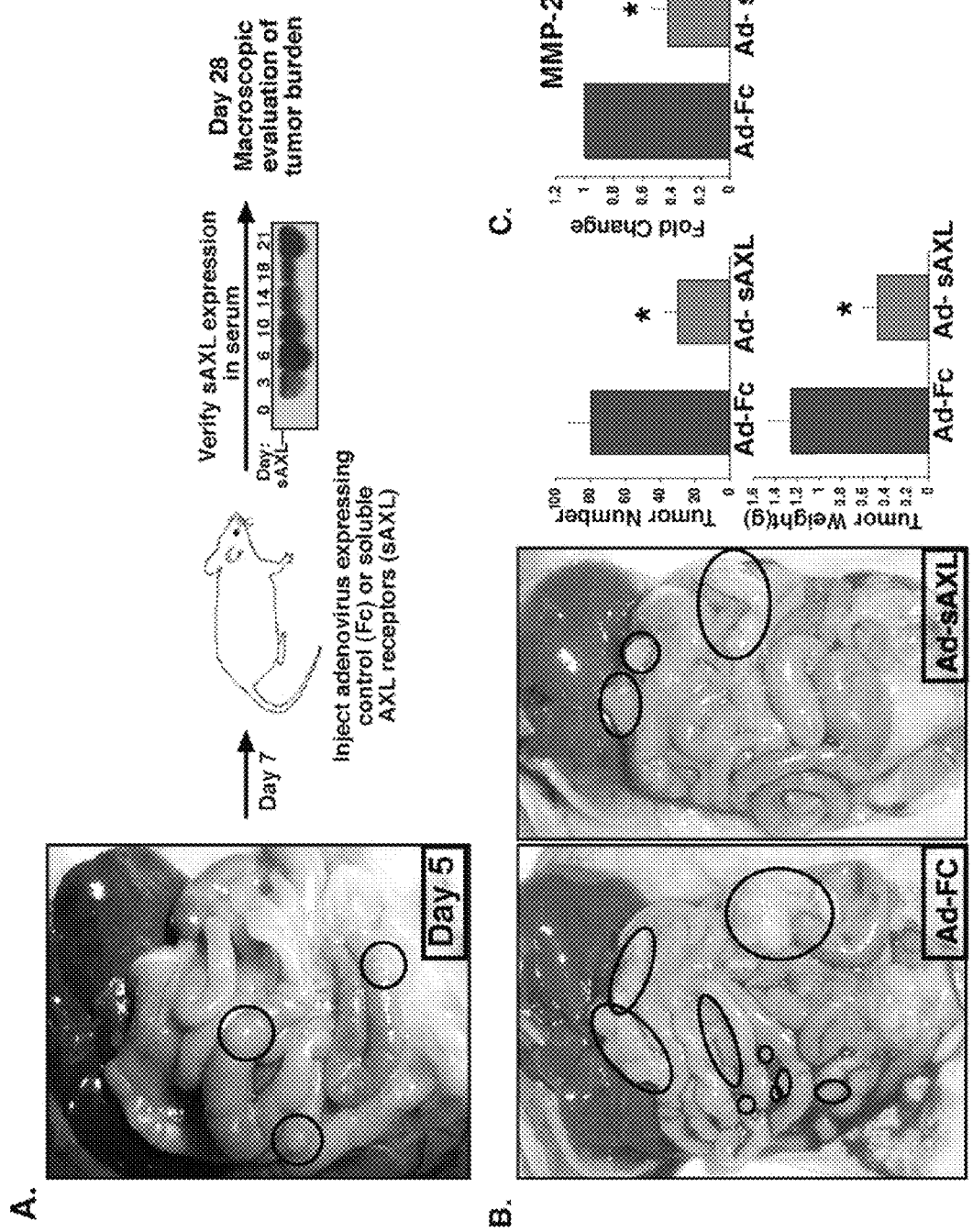
FIG. 6. Treatment with soluble AXL receptors inhibits metastatic tumor burden in mice with established metastases. A. Schematic representation of the soluble AXL receptor treatment study. Nude mice were i.p. injected with 1×10$^6$ SKOV3ip.1 cells. Five days after implantation, the presence of macroscopic lesions was verified in mice (shown is a representative photograph of a mouse with peritoneal metastasis at day 5 following injection, metastatic lesions are circled). At day 7, mice were injected with adenoviruses expression the IgG2a-Fc control (Ad-Fc) or soluble AXL receptor (Ad-sAXL). Serum levels of sAXL expression was assessed by western blot analysis every 3-4 days following adenoviral injection. Day 28 following tumor cell implantation tumor burden was assessed in all mice. B. Representative photographs of mice treated with adenoviruses expressing Ad-sAXL or Ad-Fc at 28 days following tumor cell injection. Metastatic lesions are circled. Graphs show the average total tumor number and weight for 7 mice per group. Error bars represent the S.E.M. Note that a statistical difference in tumor number and weight (p=0.01, students t test) was observed between Ad-Fc and Ad-sAXL treated mice (*). C. Real time PCR analysis of MMP-2 expression in tumors of mice treated with Ad-Fc or Ad-AXL.
Figure 11:
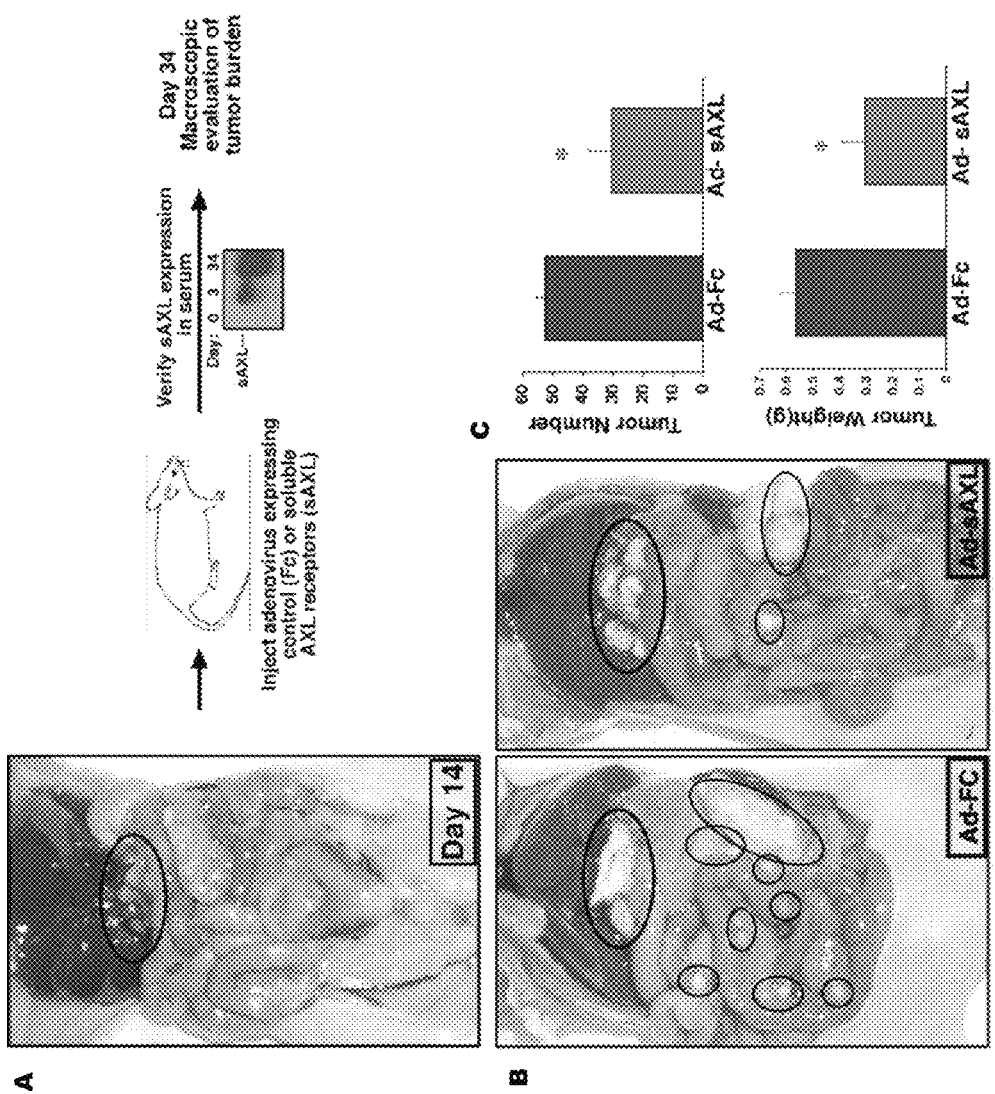
FIG. 11. Treatment with soluble AXL receptors inhibits metastatic tumor burden in mice with established OVCAR-8 metastases. A. Schematic representation of the soluble AXL receptor treatment study. Nude mice were i.p. injected with $5 \times 10^6$ OVCAR-8 cells. Fourteen days after implantation, the presence of macroscopic lesions was verified in mice (shown is a representative photograph of a mouse with peritoneal metastasis at day 14 following injection, metastatic lesions are circled). At day 14, mice were injected with adenoviruses expression the IgG2α-Fc control (Ad-Fc) or soluble AXL receptor (Ad-sAXL). Serum levels of sAXL expression was assessed by western blot analysis. Day 34 following tumor cell implantation tumor burden was assessed in all mice. B. Representative photographs of mice treated with adenoviruses expressing Ad-sAXL or Ad-Fc at 28 days following tumor cell injection. Metastatic lesions are circled. C. Graphs show the average total tumor number and weight for 8 mice per group. Error bars represent the S.E.M. Note that a statistical difference in tumor number and weight ($p<0.01$, students t test) was observed between Ad-Fc and Ad-sAXL treated mice (*).

We next examined whether sAXL treatment would affect metastatic tumor progression in the highly metastatic models of ovarian cancer. We first established SKOV3ip.1 metastatic lesions in nude mice (day 1) and began treatment with sAXL at day 7 following verification of macroscopic lesions. sAXL therapy was delivered using the adenoviral system in which the liver releases systemic production of sAXL protein into the serum of mice for up to 28 days following injection (FIG. 6A). Macroscopic analysis of tumor burden at day 28 revealed that mice receiving sAXL therapy had a significant ($p<0.01$) reduction in tumor burden compared to mice treated with the Fc control therapy. In the SKOV3ip.1 tumor model, total tumor weight and tumor number was decreased by 63% in mice treated with sAXL compared to Fc treated mice (FIG. 6B). Similarly in the OVCAR-8 model, total tumor weight and tumor number was significantly decreased by 47% and 42% respectively (FIG. 11). We examined MMP2 expression levels in SKOV3ip.1 tumors by real time PCR analysis and found that MMP2 levels were significantly decreased in the tumors of sAXL treated mice compared to Fc control treated mice (FIG. 6C). These results demonstrate that single agent AXL therapy is sufficient to significantly reduce metastatic tumor burden in mice with established disease. In addition, our findings suggest that the therapeutic effect of AXL on metastatic tumor growth may involve the inhibition of invasion at least in part through the regulation of MMP activity.

Figure 7:
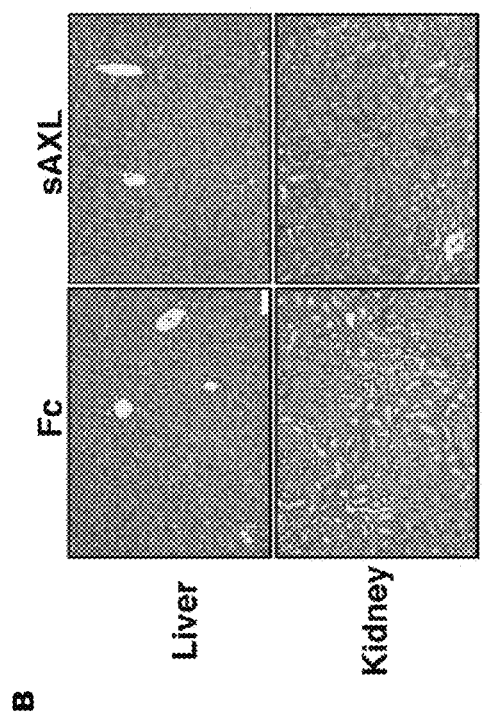
FIG. 7. Soluble AXL ectodomain therapy does not induce normal tissue toxicity. A. Complete CBC and serum chemistry analysis of mice treated with control (Fc) or soluble AXL therapy (sAXL). B. H&E staining of liver and kidney tissue collected from mice treated with Fc or sAXL.

Given that previous anti-metastatic inhibitors that target MMPs have been shown to have significant effects on normal tissue toxicity, we performed a comprehensive analysis of normal tissue toxicity in mice treated with sAXL therapy for 21 days. We observed no behavioral, macroscopic, or microscopic abnormalities in nude mice treated with sAXL or Fc therapy (FIG. 7).

Invasion and migration are important cell intrinsic properties that contribute to the pathogenesis of tumor metastasis. It has been hypothesized that therapeutic agents targeting these processes may be a useful strategy to inhibit metastasis and may provide clinical benefits to patients with metastatic disease. In this report, we demonstrate that the receptor tyrosine kinase AXL is a critical factor governing tumor cell invasion and metastasis. Most importantly, we show that therapeutic blockade of AXL signaling using soluble AXL receptors is sufficient to significantly inhibit metastatic tumor progression in mice with pre-existing metastatic disease. Mechanistically, our studies indicate that soluble AXL therapy inhibits tumor metastasis at least in part through the inhibition of MMP activity and invasion. Finally, we show that AXL is highly expressed in metastases and advanced stage primary tumors from human ovarian and breast cancer patients highlighting the clinical importance of our findings.

It is demonstrated herein that AXL is a critical factor for metastasis in human cancer and that therapeutic blockade of AXL signaling is an effective treatment for metastatic disease. Here we demonstrate that AXL is highly expressed in metastases and advanced primary tumors samples from breast and ovarian cancer patients. We demonstrate genetically that AXL is critical for the initiation of metastatic breast and ovarian cancer using disease using nude mouse models. Most importantly, we have developed highly specific and non-toxic soluble AXL receptors as an anti-AXL therapy and demonstrate that soluble AXL receptor therapy is sufficient to significantly inhibit metastatic tumor progression in mice with pre-existing metastatic disease. Our findings demonstrate that inhibition of the AXL signaling cascade in tumor cells can block both the initiation and progression of metastatic disease. Our data implicate AXL as a new therapeutic target for advanced and metastatic breast and ovarian cancer and suggest that anti-AXL therapy may control both the initiation and progression of metastatic disease.

Figure 8:
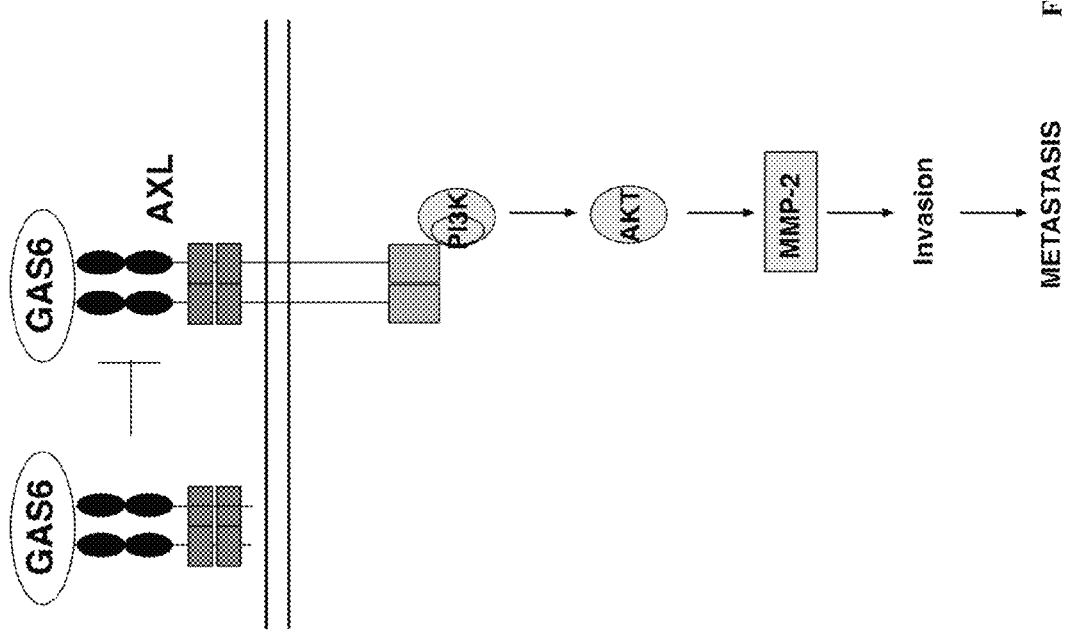
FIG. 8. Schematic diagram illustrating the molecular mechanisms associated with soluble AXL receptor inhibition of metastasis. Soluble AXL receptor (sAXL) therapy functions as a decoy receptor that binds to the AXL ligand GAS6. sAXL inhibits endogenous GAS6-AXL signaling events that stimulate cellular invasion and metastasis.

MMPs play an important role in the regulation of tumor cell invasion and metastasis. However, the mechanisms by which tumor cells induce MMP activity remain unclear. MMP expression is increased in human cancer and correlates with tumor progression and poor patient survival. Gene amplifications and activating mutations in MMPs are rarely found in human cancer suggesting that other factors are responsible for enhanced MMP expression in cancer. Our data provide evidence that MMP-2 expression is regulated by AXL at the transcriptional level in human ovarian cancer cells. While the exact mechanisms by which AXL regulates MMP-2 expression remain to be determined, we demonstrate that pharmacological inhibition of the PI3K pathway reduces MMP-2 promoter activity in GAS6 stimulated cells indicating a role for the PI3K pathway (FIG. 8). Importantly, our results indicate that therapeutic blockade of AXL may be an effective and non-toxic strategy to inhibit MMP activity in tumors. Broad-spectrum MMP inhibitors were unsuccessful in cancer trials in part due to high levels of normal tissue toxicity. Our findings indicate that predicted side effects of anti-AXL therapy are minimal. We did not observe any normal tissue toxicity associated with adenoviral-mediated delivery of soluble AXL ectodomain therapy in mice. Furthermore, germline AXL and GAS6 knockout mice are viable and phenotypically normal as adults suggesting that AXL or GAS6 are not required for development or normal tissue function.

We show that single-agent AXL therapy is sufficient to inhibit metastatic tumor progression in highly metastatic models of metastatic ovarian cancer. These findings have important clinical implications for the treatment of ovarian cancer. Approximately 14,600 people die from ovarian cancer each year in the United States. Currently there are no FDA approved biologics for the treatment of ovarian cancer, although Avastin (mAb targeting VEGF) and Tarceva (small molecule EGFR kinase inhibitor) are in clinical trials for the treatment of advanced and recurrent ovarian cancer. Standard therapy for ovarian cancer includes surgery with optimal debulking of disease followed by cytotoxic platinum-taxane combination therapy. Despite these efforts, eighty percent of patients diagnosed with ovarian cancer develop recurrent disease and only 30% of these patients survive 5 years following diagnosis.

Our data show that AXL therapy is an effective adjuvant therapy for the treatment of advanced and recurrent ovarian cancer. The model of metastatic ovarian tumor progression used in our studies resembles the development of recurrent disease in human patients following surgical debulking. We found that AXL therapy was able to reduce metastatic tumor burden in mice with established disease by 63% (using the adenovirus delivered wild type AXL). The establishment of new metastatic lesions during the progression of disease was significantly reduced. This observation is consistent with our findings demonstrating that AXL predominantly affects tumor cell invasion rather than cellular proliferation or growth. Taken together our results indicate that AXL therapy functions primarily as an anti-metastatic agent and may be most effective as a combination therapy with current cytotoxic agents.

In summary, AXL is a critical factor for metastasis and blockade of AXL signaling has therapeutic benefits in metastasis. These studies provide important pre-clinical data for anti-AXL therapy for metastatic disease.

Methods

Cell Lines. Ovarian SKOV3, SKOV3ip.1, and HEYA8 cells were obtained as a gift from Dr. Gordon Mills (MD Anderson Cancer Center). Ovarian ES-2 and MESOV cells were a gift from Dr. Branimir Sikic (Stanford University). MDA-231, OVCAR-3, and MCF-7 cells were purchased from ATCC. IGROV-1 and OVCAR-8 cells were purchased from the NCI-Frederick DCTD tumor cell line repository. Cells were cultured in the appropriate media supplemented with 10% heat inactivated fetal bovine serum and 1% penicillin and streptomycin at 37° C. in a 5% $CO_2$ incubator. Cell pellets from the NCI60 panel of breast and ovarian cancer cell lines were provided by Dr. Giovani Melillo (NCI-Frederick).

Patients and Tissue Microarrays. Human breast tissue microarrays were purchased from US Biomax (BR1002). Ovarian human tissue microarrays were obtained from the Stanford University Pathology Department. A total of 73 paraffin embedded tumor samples were obtained from previously untreated ovarian cancer patients at Stanford Hospital from 1995 to 2001. These primary ovarian tumor samples were assembled into a tissue microarray consisting of two samples per patient. An additional 30 tumor samples from the peritoneum were also evaluated in this microarray. All patients had serous ovarian cancer, and staging information was obtained according to the International Federation of Gynecology and Obstetrics standards. All specimens and their corresponding clinical information were collected under protocols approved by the institutional review board at Stanford University. An additional commercially available tumor microarray was used to examine 32 metastatic lesions from the omentum (US Biomax).

AXL Immunohistochemistry. Paraffin embedded tissue slides were deparaffinized with xylene, rehydrated, and unmasked following standard immunohistochemical methods. The AXL primary antibody (RandD Systems) was used at a 1:500 dilution. Negative controls for all samples were done using the secondary antibody alone. Antigen-antibody complexes were visualized using the VECTASTAIN ABC system (Vector Laboratories) and DAB Substrate Kit for Peroxidase (Vector Laboratories) following the protocols of the manufacturer. Slides were counterstained with hematoxylin. AXL staining on the membrane of tumor cells was scored microscopically according to the percentage of cells positive for AXL expression (0 for absence, 1 for poor quality sample, 2 for 5-60%, and 3 for 61-100%).

Reporter Assays. The MMP-2 reporter plasmid driven by 1659 bp of the MMP-2 promoter was a gift. Luciferase activity was determined by Dual-Glo Luciferase Assay reagent (Promega) in shSCRM and shAXL SKOV3ip.1 cells and measured in a Monolight 2010 Luminometer (Analytical Luminescence Laboratory). Firefly luciferase activity was normalized to *Renilla* activity. Assays were performed in triplicate and were repeated twice.

Transient and Retroviral Transfections. Transient DNA transfections were performed with Lipofectamine 2000 (Invitrogen) in accordance with the manufacturers instructions. 0.1 µg of MMP-2 cDNA (OpenBiosystems) was transfected into a 6 well dish.

siRNA: siRNA sequences targeting AXL or control were purchased form Dharmacon. All siRNA transfections were carried out using Dharmacon Smart Pools with Dharmafect 1 transfection reagent according to manufacturer's protocol (Dharmacon, Lafayette, Colo.).

shRNA: Oligos for the specific degradation of AXL RNA were synthesized as previously described [SEQ ID NO:8] 5'-GATTTGGAGAACACACTGA-3'. A scramble sequence was used as a non-targeting shRNA [SEQ ID NO:9] 5'-AAT-TGTACTACACAAAAGTAC-3'. These oligos were cloned into the RNAi-Ready pSiren RetroQ (BD Bioscience) vector and SKOV3ip. 1, MDA-231, and OVCAR-8 cells were retrovirally transduced with these vectors. Infected cells were selected in puromycin (Sigma) and polyclonal populations were tested for decrease AXL expression levels by western blot analysis.

Plasmids. The AXL ectodomain corresponding to amino acids 1-451 was amplified from the human AXL cDNA (Open Biosystems) and cloned into the CMV-driven pADD2 adenoviral shuttle vector. Transient DNA transfections with control vector or AXL 1-451 were performed with Lipofectamine 2000 (Invitrogen) in accordance with the manufacturers into HCT116 cells. Conditioned media was collected 48-72 hours following transfection.

Adhesion Assays. SKOV3ip.1 shSCRM and shAXL cells were fluorescently labeled with 5 um CMFDA (Molecular Probes). Cells were washed and detached using a non-enzymatic cell dissociation buffer (Gibco). Cells (5×10e5) were plated into a 96 well plate and precoated with 50 ug/ul of collagen type I (BD Bioscience). After a 60-minute incubation at 37 C, cells were carefully washed 5 times. Fluorescent activity (excitation, 494 nm; emission, 517 nm) was measured using a fluorescent spectrophotometer.

SKOV3ip.1 Adhesion to Collagen TypeI. SKOV3ip.1 shSCRM and shAXL cells were fluorescently labeled with 5 um CMFDA (Molecular Probes). Cells were washed and detached using a non-enzymatic cell dissociation buffer (Gibco). Cells (5×10e5) were plated in triplicate into a 96 well plate and precoated with 50 ug/ul of collagen type I (BD Bioscience). After a 60-minute incubation at 37 C, cells were carefully washed 5 times. Fluorescent activity (excitation, 494 nm; emission, 517 nm) was measured using a fluorescent spectrophotometer.

MDA-231 Adhesion to ECM Proteins. MDA-231 shSCRM and shAXL (0.5×10^6) cells were plated in triplicate onto wells containing an array of ECM proteins including laminin, collagen I and IV, fibronectin, and fibrinogen. Cells were incubated at 37 C for 1 hr and washed in PBS. Adherent cells were stained and quantified at OD 560 according to the manufacturer's protocol (CellBiolabs).

Migration Assays. Cellular migration was examined in vitro as previously described. Briefly, cells were serum-deprived for 24 hr and seeded ($2.5 \times 10^4$ cells) in triplicate onto uncoated inserts (BD Biosciences), moved to chambers containing FBS as chemo-attractant and incubated for 24 hr. After removing the non-invading cells, the cells at the bottom side of the membranes were fixed, stained and counted. Five fields were counted for each membrane. The % migration was determined as follows: (average # of cells migrating in shAXL cells/average # of cells migrating in shSCRM cells)×100. Experiments were performed in triplicate and repeated three times.

Collagen Invasion Assay. Collagen invasion assays were performed as previously described. Briefly, 533 cells were plated into collagen type I on a 48 well plate. Cells were cultured in standard media or media with the addition of conditioned control media or sAXL-conditioned media for 5-7 days and photographs were taken. Invasion through collagen was quantified by calculating the percentage of tumor cells that displayed a branching phenotype per 20× field. Three fields per sample were counted. Experiments were performed in triplicate and repeated 2 times.

Gelatin Substrate Zymography. SKOV3ip.1 shSCRM and shAXL cells were serum starved for 48 hours. 25,000 cells were plated into a 96 well plate and conditioned media was collected 24 hours later. Equal volumes of conditioned media were run under non-reducing conditions on 10% zymogram gels (Invitrogen). After electrophoresis, gels were washed in 2.5% (v/v) Triton X-100 to remove SDS and washed in 50 mM Tris-HCl, 5 mM $CaCl_2$, and 0.1% Triton X-100 (pH 7.8) and incubated overnight at 37° C. Zymograms were stained for 30 min with 0.25% (w/v) Coomassie Brilliant Blue R250 dissolved in 40% methanol and 10% glacial acetic acid. Gels were distained in 40% methanol and 10% glacial acetic acid. Experiments were performed in duplicate and repeated three times.

Cell Proliferation Assays. For monolayer growth curves, cells (50,000) were plated into 60 mm dishes in triplicate. Every three days, the cells were trypsinized, counted using a cell counter (coulter counter) and 50,000 cells were replated and counted.

XTT Survival Assay. Cell viability was measured by the XTT assay as previously described. Briefly, serum fed or starved cells (0, 3, 6, and 7 days) were incubated with phenol red-free medium with 0.3 mg/mL XTT and 2.65 μg/mL N-methyl dibenzopyrazine methyl sulfate. The 96-well plates were returned to the 37° C. incubator for 1 to 2 h. Metabolism of XTT was quantified by measuring the absorbance at 450 nm.

Protein Isolation and Western Blot Analysis. Protein lysates were harvested in 9M Urea, 0.075M Tris buffer (pH 7.6). Protein lysates were quantified using the Bradford assay, and subjected to reducing SDS-PAGE using standard methods. Western blots were probed with antibodies against AXL (RandD Systems), alpha Tubulin (Fitzgerald Antibodies), AKT (Cell Signaling), phospho-AKT (Cell Signaling).

For GAS6 stimulation, cells were serum starved for 24 hours. Cells were then treated with 25 um of PI3K inhibitor (Ly294002, Bio Mol Research Laboratory) or 100 l of conditioned media containing the AXL Ecto domain for 4 hours before treatment with 400 ng/ml of GAS6 for 15 minutes.

For analysis of sAXL expression in the serum of mice, 1.5 l of serum from each samples was analyzed by gel electrophoresis.

Generation and Production of Adenovirus. The AXL ectodomain corresponding to amino acids 1-451 was amplified from the AXL cDNA (Open Biosystems) and cloned into the E1 region of E1⁻E3⁻ Ad strain 5 by homologous recombination followed by adenovirus production in 293 cells and CsCl gradient purification as previously described. The production and purification of the sAXL adenovirus was performed as previously described. The generation and production of the negative control virus expressing murine IgG2-Fc immunoglobulin fragment has been previously described.

Growth of SKOV3ip.1 and OVCAR-8 Cells as Peritoneal Xenografts. All procedures involving animals and their care were approved by the Institutional Animal Care and Usage Committee of Stanford University in accordance with institutional and NIH guidelines.

Control and AXL SKOV3ip.1 and OVCAR-8 cells were injected i.p. with $1 \times 10^6$ and $5 \times 10^6$ cells respectively in 0.5 ml of PBS into female nude mice. After sacrifice, ascites was quantified, metastatic lesions were counted, and all visible lesions were dissected and removed to weigh tumor weight.

SKOV3ip.1 and OVCAR-8 parental cells were injected i.p. with $1 \times 10^6$ and $5 \times 10^6$ cells respectively in 0.5 ml of PBS into female nude mice. Seven (SKOV3ip.1) or 14 (OVCAR-8) days following tumor cell injection, mice were injected with sAXL or control $1.9 \times 10^8$ adenoviral pfu in 0.1 ml PBS into the tail vein. After sacrifice, ascites was quantified, metastatic lesions were counted, and all visible lesions were dissected and removed to weigh total tumor weight.

Tissue Toxicity Studies. SKOV3ip.1 parental cells were injected i.p. with $1 \times 10^6$ and $5 \times 10^6$ cells respectively in 0.5 ml of PBS into female nude mice. Seven days following tumor cell injection, mice were injected with sAXL or control $1.9 \times 10^8$ adenoviral pfu in 0.1 ml PBS into the tail vein. At day 28, mice were sacrificed. Blood was collected and a comprehensive metabolic panel and CBC analysis was performed by the Department of Comparative Medicine at Stanford University. Tissue samples were collected from all major organs including liver, kidney, brain, and spleen, fixed in 10% formalin, embedded in paraffin, sectioned, and counter stained with hematoxylin and eosin.

In vivo Tail-Vein Metastasis Assay. Control and AXL shRNA MDA-231 cells were injected intravenously with $5 \times 10^5$ cells in 0.1 ml of PBS into the tail vein of nude mice. Four weeks after injection, mice were sacrificed. Microscopic evaluation of lung foci was performed on representative cross-sections of formalin-fixed, paraffin-embedded lungs stained with haematoxylin and eosin. The correct identification of lung foci with a minimum of four human cells with large nuclei and positive for AXL expression was confirmed by a board-certified pathologist. Tumor burden in the lungs of mice was quantified by real time PCR analysis of human GAPDH and AXL expression in RNA isolated from whole lung.

Growth of MDA-231 Cells as Orthotopic Tumors. MDA-231 cells were grown as subcutaneous orthotopic tumors in six-week-old female Nude (nu/nu) mice after intradermal injection of $10^7$ cells in 0.1 ml of PBS into the mammary fat pad. Tumors were measured with calipers over a 38-day time course. Volume was calculated using the following formula: $width^2 \times length \times 0.5$.

Growth of SKOV3ip.1 Cells as Subcutaneous Tumors. Five million cells in 0.1 ml of PBS were implanted subcutaneously into the flanks Nude (nu/nu) six-week-old female mice. Tumors were measured with calipers over a 45-day time course. Volume was calculated using the following formula: width$^2$×length×0.5.

RNA and Real Time PCR Analysis. RNA was isolated from cells and tissues using trizol according to manufacturer's protocols (Invitrogen), cDNA was synthesized from 2 μg of DNase (Invitrogen)-treated RNA using the SuperScript first-strand synthesis system for reverse transcription-PCR (Invitrogen). One microliter of cDNA was subjected to PCR amplification using SYBR GREEN PCR Master Mix (Applied Biosystems). The following primer sets were used to amplify specific target genes: 18S FWD: [SEQ ID NO:10] 5-GCCCGAAGCGTTTACTTTGA-3 REV: [SEQ ID NO:11] 5-TCCATTATTCCTAGCTGCGGTATC-3; AXL FWD: [SEQ ID NO:12] 5-GTGGGCAACCCAGG-GAATATC-3 REV: [SEQ ID NO:13] 5-GTACTGTCCCGT-GTCGGAAAG; GAPDH [SEQ ID NO:14] 5-ATGGG-GAAGGTGAAGGTCG-3 REV: [SEQ ID NO:15] 5-GGGGTCATTGATGGCAACAATA-3; MMP-2 FWD: [SEQ ID NO:16] 5-GCCCCAGACAGGTGATCTTG-3 REV [SEQ ID NO:17] 5-GCTTGCGAGGGAAGAAGT-TGT-3. PCR amplification was performed on the Prism 7900 Sequence Detection System (Applied Biosystems). The thermal-cycling profile used was denaturation at 50° C. for 2 min and 95° C. for 10 min, followed by cycles of denaturation at 95° C. for 15 s and 60° C. for 1 min. 18 S was used to normalize mRNA. Relative mRNA expression levels were determined using the relative standard curve method according to the manufacturer's instructions (Applied Biosystems).

Statistical Analysis. Tests for an association between AXL expression and tumor formation and metastasis was performed using the Fisher's exact test. All other statistical tests were performed using the Student's t test. Values with a p value of <0.05 were considered statistically significant.

Abbreviations: GAS6, growth arrest specific gene 6; MMP-2, matrix metalloproteinase; EOC, epithelial ovarian cancer; ECM, extracellular matrix; AKT, v-akt murine thymoma viral oncogene homolog.

TABLE 1

Statistical Analysis of AXL Staining to Tumor Parameters

| | Score | | | | |
|---|---|---|---|---|---|
| | 0 | 1 | 2 | 3 | Total |
| Breast Infiltrating ductal carcinoma | | | | | |
| Grade 1 | 3 (75) | 0 (0) | 0 (0) | 1 (25) | 4 |
| Grade 2 | 3 (23) | 0 (0) | 5 (38) | 5 (38) | 13 |
| Grade 3 | 0 (0) | 0 (0) | 7 (39) | 11 (61) | 18 |
| Totals | 6 | 0 | 12 | 17 | 35 |
| Pearson X2 P value = Metasatic Infiltrating ductal carcinoma | | | | | |
| Lymph node Ovarian Serous adenocarcinoma | 0 (0) | 1 (11) | 4 (44) | 4 (44) | 9 |
| Stage II | 3 (33) | 0 (0) | 3 (33) | 3 (33) | 9 |
| Stage III/IV | 6 (9) | 5 (8) | 14 (22) | 39 (61) | 64 |
| Totals | 9 | 5 | 17 | 42 | 73 |

TABLE 1-continued

Statistical Analysis of AXL Staining to Tumor Parameters

| | Score | | | | |
|---|---|---|---|---|---|
| | 0 | 1 | 2 | 3 | Total |
| Pearson X2 P value = Metasatic serous adenocarcinoma | | | | | |
| Omentum | 3 (9) | 5 (16) | 6 (19) | 18 (56) | 32 |
| Peritoneum | 1 (3) | 2 (7) | 12 (40) | 15 (50) | 30 |
| Totals | 4 | 7 | 18 | 33 | 62 |

Values are represented as n (%).
For tumor cells, membranous staining was scored as 0, absence; 1, unable to score; 2, 5 to 60% positive; 3, 61 to 100% positive.

Example 2

We showed that inhibition of the GAS6 ligand binding to cellular AXL through overexpression of wild-type soluble AXL in mice using an adenoviral expression system resulted in decreased tumor burden, as measured by tumor number and size, compared to untreated control, further highlighting the importance of GAS6 and AXL as critical targets and effective strategies to inhibit the progression of metastasis in pre-clinical mouse models.

Engineered soluble variants of the AXL extracellular domain are provided herein, which have high affinity for the ligand GAS6, allowing them to sequester the ligand and diminish endogenous AXL signaling. Engineered variants have substantially improved affinity for Gas6 compared to wild-type AXL.

The extracellular domain of AXL comprises two IgG-like domains and two fibronectin-like domains. The major GAS6 binding site is in the Ig1 domain, and the minor GAS6 binding site is in the Ig2 domain.

To further enhance the affinity of the major binding site, we engineered the Ig1 domain with break points of 19-132 corresponding to the AXL SwissProt entry P30530. A mutant library was created by performing error-prone PCR on the Ig1 domain of the AXL receptor using standard molecular biology techniques. The library was expressed using yeast surface display and screened by fluorescence-activated cell sorting (FACS) to isolate mutants which exhibit enhanced binding affinity to soluble GAS6. In our library screening approach, the mutant protein library was subjected to multiple rounds of sorting wherein each successive round reduces the size of the library while concurrently enriching for desired mutant protein property, which in this case is high affinity binding to GAS6.

In order to obtain AXL mutants with significantly strong affinity for GAS6, in the later sorting rounds we used "off-rate" sorts. For off-rate sorts, the library of protein mutants is first incubated with soluble GAS6 and then washed with buffer to remove unbound GAS6 from the solution. Next, the mutant library is incubated in the presence of excess soluble competitor for 2, 4, 6, 12, or 24 hr at room temperature. The excess competitor serves to sequester GAS6 that dissociates from yeast-displayed AXL, rendering the unbinding step irreversible. Mutant AXL proteins that retain binding to GAS6 are collected using FACS. Analysis of the binding to GAS6 by the pooled sort 5 products following off-rate steps of 0, 4 and 6 hours shows these products exhibit significant improvement over wild-type AXL in terms of persistent binding to GAS6

Figure 12B:
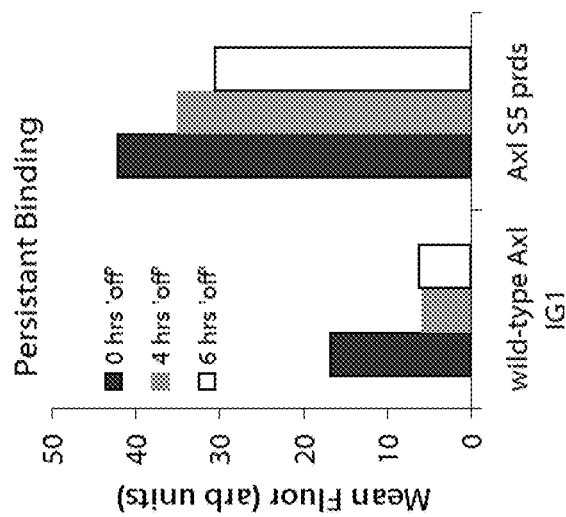
FIG. 12. Binding of AXL Library sort 5 products to GAS6. Flow cytometry dot plots of yeast cells expressing either wild-type AXL (A) or the pooled AXL Sort 5 products from the directed evolution work (B). Data shows binding following off-rate tests as described in Example 2. Levels of binding to 2 nM Gas6 are shown in the left column, levels of binding to Gas6 following a 4 hour unbinding step are shown in the middle column, and levels of binding to Gas6 following a 6 hour unbinding step are shown in the right column. For cells that are positive for expression of the particular protein on its cell surface (upper right quadrant of each flow cytometry dot plot), binding levels to Gas6 (y-axis) are quantified in the bar graph below. The pooled Sort 5 products show significantly improved Gas6 binding compared to wild-type AXL.

(see FIG. 12). The bar graph quantifies the data from the dot plots, demonstrating significant improvement of the library members. Sequencing of these products identified several mutations within the Axl Ig1 domain that confer the enhanced affinity towards Gas6 observed for the pooled sort 5 products (FIG. 12 and Table 2). A 6$^{th}$ round of sorting further enriched to 3 specific clones from the sort 5 products. Table 2 shows unique amino acid mutations within the AXL sequence that are contained in the sort round 5 and round 6 products. In this table, the residue number in the top row indicates the amino acid residue in wild-type AXL. The second row indicates the residue found in wild-type AXL at the given position. In subsequent rows, amino acid mutations present in the given mutant are specified. Absence of an amino acid for a particular residue within a mutant (e.g. a blank space or a blank cell in Table 2) denotes that this amino acid residue is not mutated from the wild-type residue. The standard single letter designation for amino acid residues is used as is well-understood by one who is skilled in the art.

Shown are unique sequences from the sort 5 and 6 products, as well as the binding properties of the pooled clones as compared to wild-type AXL, demonstrating substantial improvement in GAS6 binding for the pooled sort 5 products.

Mutants isolated using this directed evolution approach include the amino acid substitutions shown in Table 3.

TABLE 3

Mutants Isolated Using Directed Evolution

|  | 26 | 32 | 33 | 74 | 79 | 87 | 92 | 127 |
|---|---|---|---|---|---|---|---|---|
| Wt-AXL | E | G | N | S | V | D | V | G |
| Axl S6-1 |  | S |  |  |  | G | A | R |
| Axl S6-2 | G |  |  |  | M |  | A | E |
| Axl S6-5 |  |  | S | N |  | G | A |  |

According to the crystal structure of the GAS6-AXL complex reported by Sasaki et al. (EMBO J 2006), all mutations shown above, except for E26G, G32S, N33S and G127R/E, lie at the binding interface between AXL and GAS6.

Figure 13:
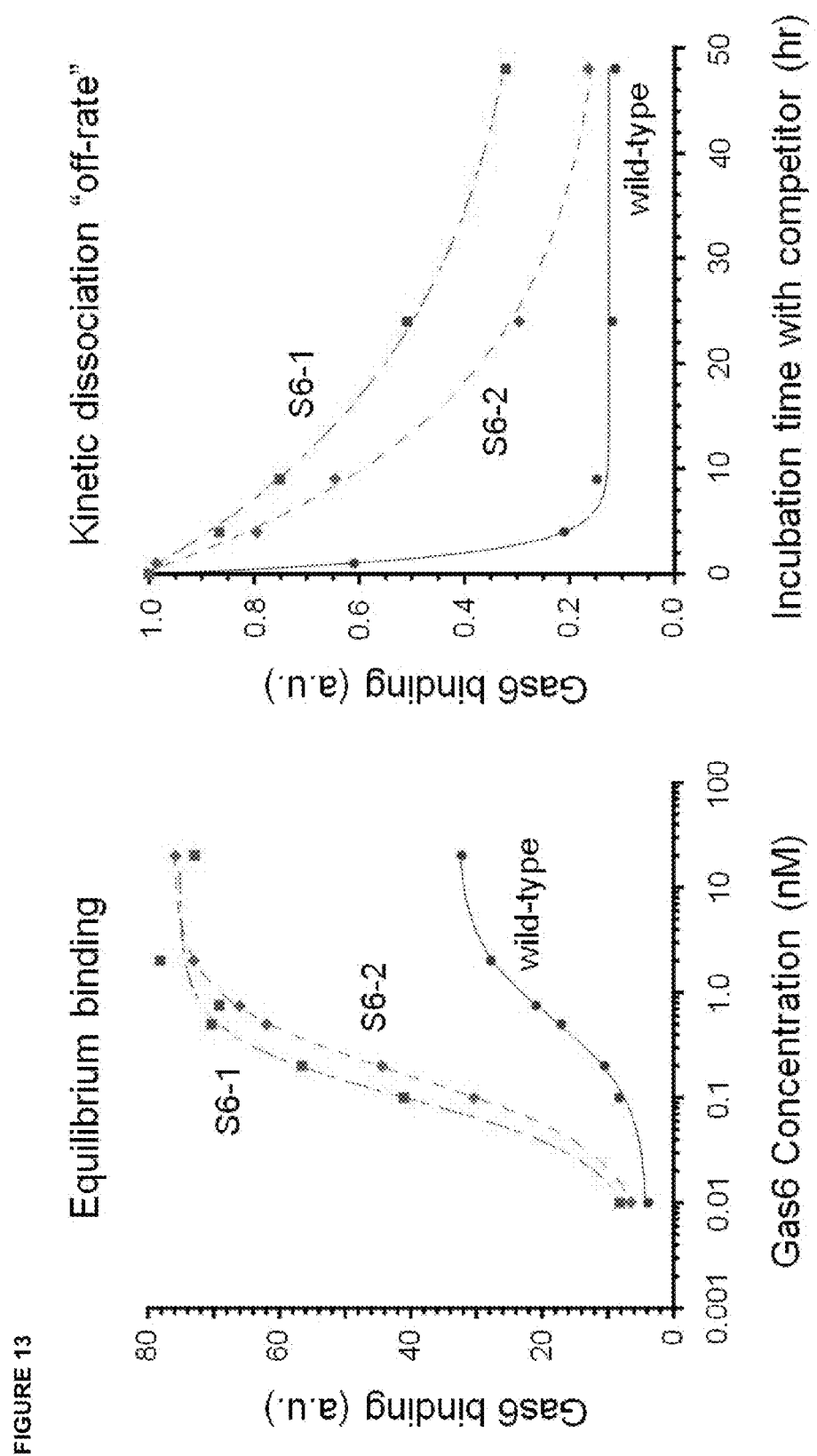
FIG. 13. Binding of enhanced AXL variants to GAS6. Left panel shows equilibrium binding towards Gas6 by the AXL mutants S6-1 (red squares) and S6-2 (blue diamonds) as compared to wild-type AXL (green circles). The mutants S6-1 and S6-2 exhibit significantly higher levels of binding to lower concentrations of Gas6, demonstrating stronger binding affinity for these mutants compared to wild-type AXL. The right panel shows dissociation kinetics of the wild-type or engineered Gas6-AXL interaction. The wild-type Gas6-AXL interaction ("wild-type") dissociates rapidly as a function of time, wild the engineered interaction between Gas6 and S6-1 ("S6-1") or S6-2 ("S6-2") shows significantly increased retention of binding.

Individual mutants, AXL S6-1 and AXL S6-2, from the sixth round of sorting were selected for further investigation. Equilibrium binding titrations of wild-type AXL, AXL S6-1, and AXL S6-2 were conducted to compare affinity of the interaction with GAS6 of the wild-type or mutant AXL proteins. The data was fit to a four-point sigmoidal curve and the midpoint was taken as the equilibrium binding constant, $K_D$. The mutants AXL S6-1 and AXL S6-2 exhibit substantial improvements in GAS6 binding affinity compared to wild-type AXL (FIG. 13 and Table 4). Wild-type AXL has a binding affinity ($K_D$) towards Gas6 of $2.4 \pm 1.2 \times 10^{-9}$ M; AXL S6-2 has a binding affinity ($K_D$) towards Gas6 of $1.89 \pm 0.37 \times 10^{-10}$ M towards Gas6; and AXL S6-1 has a binding affinity ($K_D$) of $1.12 \pm 0.23 \times 10^{-10}$ M towards Gas6. For AXL S6-1 and AXL S6-2, this is a 22-fold and 12.8-fold stronger GAS6 binding affinity, respectively, compared to wild-type AXL (Table 4).

TABLE 4

Binding affinity ($K_D$) of wild-type and mutant AXL proteins to Gas6. Equilibrium Gas6 Binding

|  | $K_D$ (M) | +/− (M) | fold over wt |
|---|---|---|---|
| wt AXL | $2.4 \times 10^{-9}$ | $1.2 \times 10^{-9}$ | — |
| S6-1 | $1.12 \times 10^{-10}$ | $0.23 \times 10^{-10}$ | 22 |
| S6-2 | $1.89 \times 10^{-10}$ | $0.37 \times 10^{-10}$ | 12.8 |

We also investigated the thermal stability of wild-type and mutant AXL proteins using variable temperature circular dichroism scans. This technique monitors the unfolding of the secondary structural elements of the folded protein as a function of temperature. Ellipticity of each protein was monitored as a function of temperature and the data was fit to a standard two-state unfolding curve. The melting temperature ($T_m$) is the midpoint of the unfolding curve. Wild-type AXL exhibited a melting temperature of $53 \pm 0.9°$ C.; AXL S6-1 exhibited a melting temperature of $54 \pm 0.9°$ C. (approximately 13° C. higher thermal stability than wild-type AXL); Axl S6-2 exhibited a melting temperature of $42 \pm 0.0°$ C. (approximately similar thermal stability to wild-type AXL) (Table 5).

TABLE 5

Thermal stability of wild-type and mutant AXL proteins as determined by variable temperature circular dichroism scans.

|  | Average Tm (° C.) | +/− (° C.) | Increase over wt (° C.) |
|---|---|---|---|
| wt AXL | 53 | 0.6 | — |
| S6-1 | 54 | 0.9 | 12.73 |
| S6-2 | 42 | 0.0 | 0.28 |

TABLE 2

AXL Ig1 mutants from Sorts 5 and 6 (141 total random clones sequenced, 25 unique variants)

| Clone | bp | AA | 19 | 23 | 26 | 27 | 32 | 33 | 38 | 44 | 61 | 65 | 72 | 74 | 78 | 79 | 86 | 87 | 88 | 90 |
|---|---|---|---|---|---|---|---|---|---|---|---|---|---|---|---|---|---|---|---|---|
| wt AXL |  |  | A | T | E | E | G | N | T | T | H | D | A | S | Q | V | Q | D | D | I |
| AXL S6-1 | 6 | 4 |  |  |  |  |  | S |  |  |  |  |  |  |  |  |  | G |  |  |
| AXL S6-2 | 5 | 4 |  |  | G |  |  |  |  |  |  |  |  |  | N |  | M |  | G |  |
| AXL S6-5 | 5 | 4 |  |  |  |  |  | S |  |  |  |  |  | N |  |  |  | G |  |  |
| AXL S5-1 | 3 | 3 |  |  |  |  |  |  |  |  |  |  | V |  |  |  |  |  |  |  |
| AXL S5-2 | 2 | 1 |  |  |  |  |  |  |  |  |  |  |  |  |  |  |  |  |  |  |
| AXL S5-4 | 1 | 1 |  |  |  |  |  |  |  |  |  |  |  |  |  |  | E |  |  |  |
| AXL S5-6 | 1 | 1 |  |  |  |  |  |  |  |  |  |  | V |  |  |  |  |  |  |  |
| AXL S5-9 | 4 | 3 |  |  |  |  |  |  |  |  |  |  |  |  |  |  | R |  |  | V |
| AXL S5-13 | 3 | 2 |  |  |  |  |  |  |  |  |  |  | V |  |  |  |  |  |  |  |
| AXL S5-22 | 2 | 2 |  |  |  |  |  |  |  |  |  | N |  |  |  |  |  | G |  |  |
| AXL S5-24 | 4 | 2 |  |  |  |  |  |  |  |  |  |  |  |  |  |  |  | G |  |  |
| AXL S5-29 | 9 | 6 |  |  |  | K |  |  |  | Y |  |  | V |  |  |  |  |  | N |  |
| AXL S5-30 | 4 | 2 |  |  |  |  |  |  |  |  |  |  |  |  |  |  |  |  |  |  |
| AXL S5-39 | 10 | 5 |  |  |  |  |  |  | A |  |  |  | V |  |  |  |  |  |  | V |
| AXL S5-40 | 3 | 1 |  |  |  |  |  |  |  |  |  |  |  |  |  |  |  |  |  |  |
| AXL S5-45 | 5 | 4 |  |  |  |  |  |  |  |  |  |  |  |  |  |  |  |  |  |  |
| AXL S5-51 | 3 | 2 |  |  |  |  |  |  |  |  |  |  |  |  |  |  |  |  |  |  |

TABLE 2-continued

AXL Ig1 mutants from Sorts 5 and 6 (141 total random clones sequenced, 25 unique variants)

| Clone | bp | AA | | | | | | | | | | |
|---|---|---|---|---|---|---|---|---|---|---|---|---|
| AXL S5-53 | 3 | 2 | | | G | | | | | | G | |
| AXL S5-59 | 3 | 2 | | | | | I | | | | | |
| AXL S5-66 | 2 | 1 | | | | | | | | | G | |
| AXL S5-68 | 5 | 2 | M | | | | | | | | | |
| AXL S5-74 | 2 | 2 | | | | | | | V | | | |
| AXL S5-76 | | 2 | | | | | | | | | R | |
| AXL S5-77 | 4 | | T | | G | G | | | | | | |
| AXL S5-78 | 2 | | | | | | | | | | | M |

| Clone | 92 | 97 | 98 | 105 | 109 | 112 | 113 | 116 | 118 | 127 | 129 | # of repeats |
|---|---|---|---|---|---|---|---|---|---|---|---|---|
| wt AXL | V | I | T | T | Q | V | F | H | T | G | E | |
| AXL S6-1 | A | | | | | | | | | R | | 62 |
| AXL S6-2 | A | | | | | | | | | E | | 21 |
| AXL S6-5 | A | | | | | | | | | | | 1 |
| AXL S5-1 | | R | | | | | | R | | | | 1 |
| AXL S5-2 | A | | | | | | | | | | | 16 |
| AXL S5-4 | | | | | | | | | | | | 1 |
| AXL S5-6 | | | | | | | | | | | | 7 |
| AXL S5-9 | A | | | | | | | | | | | 10 |
| AXL S5-13 | D | | | | | | | | | | | 1 |
| AXL S5-22 | | | | | | | | | | | | 1 |
| AXL S5-24 | A | | | | | | | | | | | 2 |
| AXL S5-29 | A | A | | | | | | | | | | 1 |
| AXL S5-30 | A | | | | R | | | | | | | 1 |
| AXL S5-39 | | | M | | | | | | | | K | 1 |
| AXL S5-40 | G | | | | | | | | | | | 2 |
| AXL S5-45 | A | | | | | A | L | | A | | | 1 |
| AXL S5-51 | A | P | | | | | | | | | | 1 |
| AXL S5-53 | | | | | | | | | | | | 1 |
| AXL S5-59 | A | | | | | | | | | | | 2 |
| AXL S5-66 | | | | | | | | | | | | 3 |
| AXL S5-68 | A | | | | | | | | | | | 1 |
| AXL S5-74 | | | | | | | L | | | | | 1 |
| AXL S5-76 | A | | | | | | | | | | | 1 |
| AXL S5-77 | A | | | | | | | | | | | 1 |
| AXL S5-78 | A | | | | | | | | | | | 1 |
| | | | | | | | | | | TOTAL READS: | | 141 |

*bp = number of DNA mismatches, AA = number of amino acid mutations.
Note some of the DNA mutations are silent.
Total number of times a particular clone showed up is indicated in the right most column.

Example 3

Soluble Axl Variants Inhibit Metastatic Tumor Progression In Vivo

GAS6-AXL signaling has been implicated in the progression of many aggressive forms of solid tumors including breast, lung, and colon and recently through work presented here, ovarian cancer. While a distinct correlation has been observed between AXL expression and disease stage and patient prognosis, validation of AXL as a therapeutic target for the treatment of metastasis has largely remained unexplored. In Example 1, we show that AXL is indeed a marker of metastasis in human breast and ovarian cancer patients, with AXL expression levels on primary tumors correlating with the severity of the disease. These results suggested that antagonizing the GAS6-AXL signaling pathway may offer a therapeutic window for treating metastatic disease. As outlined in Example 1, to validate the potential of AXL as a therapeutic target, a soluble form of the wild-type extracellular domain of AXL was administered using adenoviral delivery in an aggressive mouse model of human ovarian cancer. We showed that tumor metastases were significantly reduced in mice which received the soluble AXL treatments as compared to controls. These data demonstrated that antagonizing GAS6-AXL signaling in tumor cells using soluble AXL could inhibit the metastatic progression of the disease. Building upon these results, we showed that engineered AXL mutants with higher affinity to GAS6 elicited greater efficacy as anti-metastatic agents, and that a more therapeutically-relevant mode of delivering soluble AXL still yielded significant results.

In this study, we used the same human ovarian cancer model outlined in Experiment 1 and administered purified soluble AXL (sAXL) variants intraperitonealy to mice with pre-existing metastatic disease. We tested both wild-type AXL and AXL S6-1, the engineered high affinity mutant, and compared both to a form of AXL, E59R/T77R, in which GAS6 binding is abolished. Our results strikingly show that the enhanced affinity of AXL S6-1 results in greater therapeutic efficacy, as a reduction in tumor burden as assessed by both number and total weight of all metastatic lesions was significantly reduced over both wild-type AXL and the negative control of AXL E59R/T77R. These findings further validate AXL and GAS6 as therapeutic targets for the inhibition of metastasis and support the engineered high affinity AXL mutant S6-1 as a potent antagonist of the GAS6-AXL signaling system.

While Example 1 demonstrates that adenoviral delivery of sAXL yielded therapeutic efficacy, this method of delivery is not clinically relevant and thus we confirmed that delivery of purified, sAXL would yield similar results. Wild-type AXL, AXL S6-1 and AXL E59R/T77R were fused to the fragment crystallizable region (Fc) of a mouse IgG2a in order to improve pharmacokinetics. The only differences between these three AXL fusion (AXL-Fc) variants are mutations found in the AXL Ig1 domain, which are outlined in Table 6A. DNA encoding the AXL-Fc proteins was cloned into the CMV-driven pADD2 adenoviral shuttle vector using EcoRI and SalI restriction sites. The pADD2 plasmid encoding these three AXL mutants was independently transfected into HEK 293 cells using the Freestyle Expression kit from Life Technologies, as described by the manufacturer. Proteins were purified from culture supernatant using Protein A affinity chromatography followed by size exclusion chromatography.

TABLE 6

| Protein name | Description |
| --- | --- |
| Wild-type AXL-Fc | Wild-type AXL extracellular domain, amino acids 19-440 fused to the Fc region of mouse IgG2a. |
| AXL S6-1-Fc | AXL-Fc fusion as above for wild-type AXL-Fc, however, the AXL Ig1 domain contains the following mutations for S6-1: G32S, D87G, V92A, G127R |
| AXL E59R/T77R-Fc | AXL-Fc fusion as above for wild-type AXL-Fc, however, the Axl Ig1 domain contains E59R and T77R mutations, which significantly diminish binding towards Gas6 |

Figure 14:
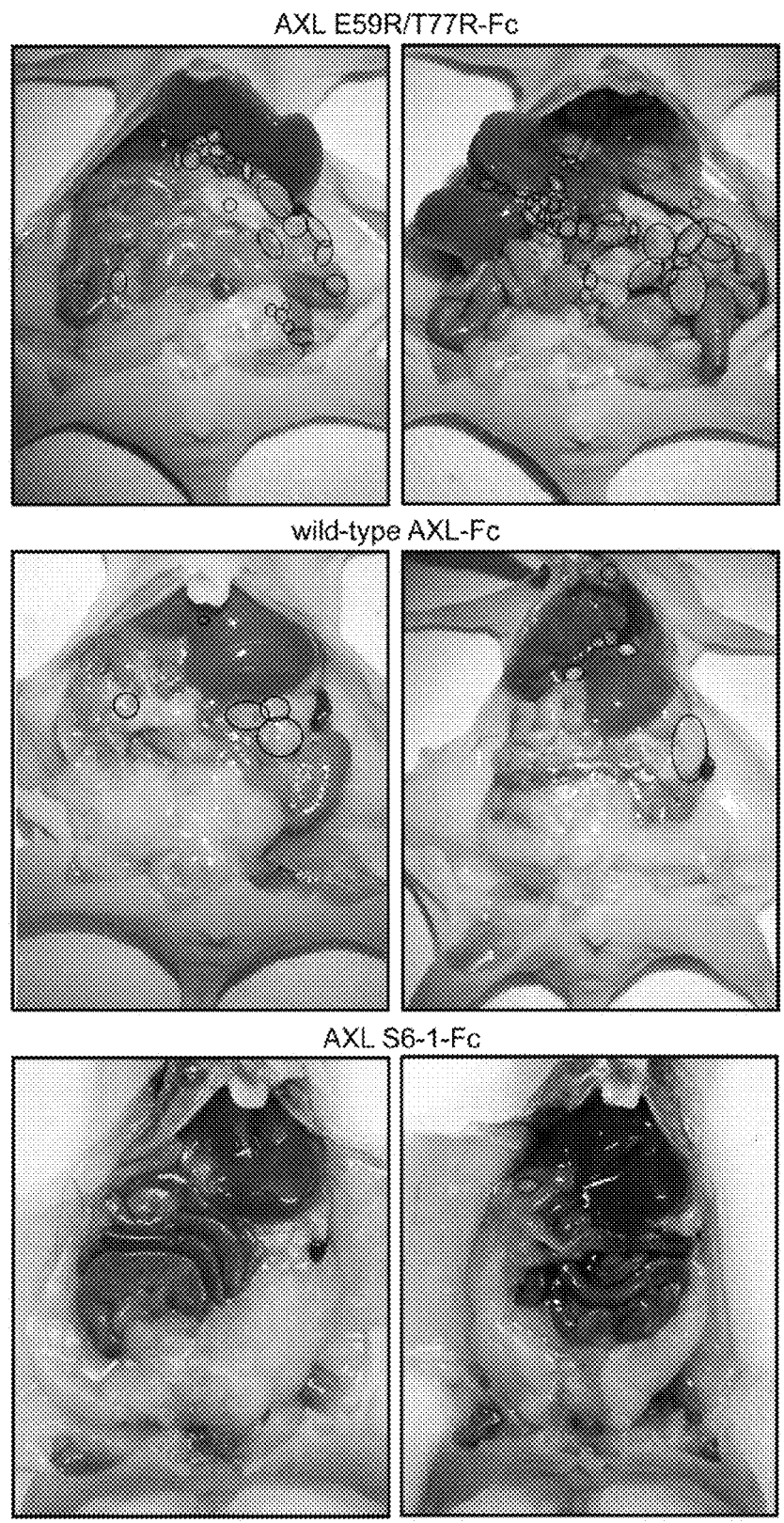
FIG. 14. Intraperitoneal delivery of purified AXL 56-1-Fc shows enhanced therapeutic effects over wild-type AXL-Fc and AXL E59R/T77R-Fc. Two representative images from the necropsies of mice from three treatment groups, AXL E59R/T77R-Fc, wild-type AXL-Fc, and AXL 56-1-Fc, are shown. Black circles indicate metastatic lesions visible in the images, but do not necessarily indicate all metastatic sites. Wild-type AXL-Fc shows moderate inhibition of metastasis over the negative control, AXL E59R/T77R, while AXL S6-1 shows nearly complete inhibition of metastasis.
Figure 15:
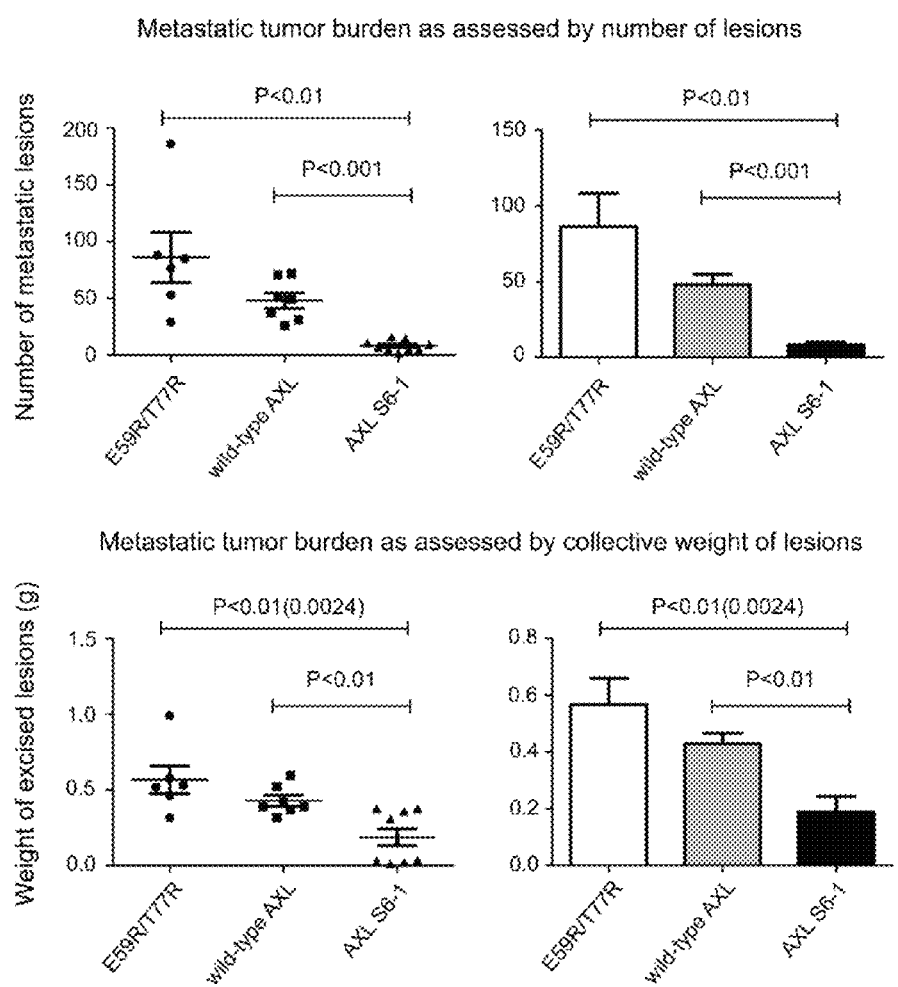
FIG. 15. Inhibition of metastasis in SKOV3ip.1 xenograph model. In the top two graphs, the same data set is presented in two different ways to indicate the average number of metastatic lesions counted in each treatment group. Similarly, the bottom two graphs show the same data set which outlines the total weight of all metastasis excised from mice in each treatment group. Wild-type AXL-Fc inhibits the spread of metastasis as compared to negative control E59R/T77R-Fc, as indicated by a decrease in both number of lesions (top panel) as well as overall weight (bottom panel). AXL S6-1-Fc shows significant reduction in tumor burden as compared to both wild-type AXL-Fc and AXL E59R/T77R-Fc as assessed by number of lesions (top panel) as well as overall weight (bottom panel). These data demonstrate that the enhanced affinity of AXL S6-1 offers improved therapeutic efficacy over wild-type and that AXL S6-1-Fc is a viable treatment for the management of metastasis.

To assess the ability of the AXL-Fc mutants to inhibit metastasis in vivo, we used the same peritoneal xenograft model of human ovarian cancer as outlined in Example 1. This model recapitulates the peritoneal dissemination of human ovarian cancer metastasis as mice rapidly develop highly invasive disease consisting of ascites and many (>100) small metastatic lesions four weeks post-administration of SKOV3ip.1 cells. This model is a very accurate representation of human ovarian cancer as most patients present with significant metastatic disease at diagnosis. Mice were injected with SKOV3ip.1 cells and tumors were allowed to seed for seven days. On day seven, we randomly split the mice into three study groups and began administering treatments of either wild-type AXL-Fc, 56-1-Fc or E59R/T77R-Fc. Purified proteins dissolved in phosphate buffered saline were administered to the mice twice a week for three weeks at a dose of 10 mg/kg, for a total of six doses. On day twenty-eight, all mice were sacrificed and necropsies were performed to assess overall tumor burden as measured by the number of visible metastatic lesions as well as the total weight of all lesions. There were profound differences between the treatment groups, and representative images are shown in FIG. 14. Mice receiving the negative control treatment of E59R/T77R-Fc had an average of 86.3±21.9 peritoneal metastases. For mice receiving wild-type AXL-Fc, that number was reduced to 48.1±6.9 while for mice in the engineered AXL group, S6-1-Fc, only 8.3±1.6 metastatic lesions were observed on average (FIG. 15 (top panel)). All visible lesions were excised and collectively weighed for each mouse to assess overall metastatic tumor burden. The engineered AXL treatment group (S6-1-Fc) again showed the most profound response, as E59R/T77R-Fc, wild-type-Fc and S6-1-Fc treatment groups exhibited tumor burdens of 567±92, 430±36 and 188±55 mg, respectively, FIG. 15 (bottom panel).

Collectively, these findings further validate AXL as a therapeutic target for the treatment of metastasis and demonstrate that neutralizing AXL's ligand, GAS6, is an effective anti-metastatic treatment strategy. Importantly, a protein comprising an AXL-Fc fusion that does not exhibit detectable binding to Gas6 (AXL E59R/T77R-Fc) does not prevent tumor metastasis; a protein comprising an AXL-Fc fusion that binds to Gas6 with moderate affinity (wild-type AXL-Fc) shows slight inhibition of tumor metastasis; a protein comprising an AXL-Fc fusion with very strong affinity to Gas6 (AXL S6-1-Fc) shows significant inhibition of tumor metastasis. Collectively, this shows that the epitope of interaction for Gas6 and AXL is critical in tumor metastasis and potent inhibition of this epitope on Gas6 through the AXL S6-1-Fc protein significantly inhibits tumor metastasis. As such, the AXL S6-1-Fc protein, or any protein that potently blocks the Gas6-Axl interaction, is a promising therapeutic candidate for metastatic disease. In addition, we also demonstrate that direct administration of purified soluble AXL protein is a viable treatment method, validating this approach clinically.

Methods for Example 3

Cell lines. Ovarian SKOV3ip.1 were cultured in the appropriate mediate supplemented with 10% fetal bovine serum and 1% penicillin and streptomycin at 37° C. in a 5% $CO_2$ incubator.

AXL-Fc fusions. Full-length AXL mutants, amino acids 19-440, were cloned into the CMV-driven pADD2 adenoviral shuttle vector as direct fusions to a mouse IgG2a Fc region. Transient DNA transfection of human embryonic kidney (HEK) 293 cells was accomplished using the Freestyle Expression kit from Life Technologies, as described by the manufacturer. Fc-fusion proteins were purified from the culture supernatant after five days using Protein A affinity chromatography and size exclusion chromatography. Purified proteins were placed in a phosphate buffered saline solution without any additional additives or carriers.

SKOV3ip.1 Peritoneal Xenographs. All procedures involving animals and their care were approved by the Institutional Animal Care and Usage Committee of Stanford University in accordance with institutional and NIH guidelines. Six week old female nude mice were injected with $1\times10^6$ SKOV3ip.1 cells intraperitonealy. Seven days after the administration of cells, mice were randomly divided into three groups for treatment with 56-1-Fc, wild-type AXL-Fc or E59R/T77R-Fc. Purified soluble AXL-Fc protein was administered via intraperitonealy injections twice a week at a dosage of 10 mg/kg. Dosing was continued for three weeks after which mice were sacrificed. Necropsies were performed in which metastatic lesions were counted and then excised to be collectively weighted. Tumor burden was determined by both the total number lesions and overall weight of all diseased tissue for each mouse.

Statistical Analysis: Student's t test was used and errors reported are standard error of the mean (SEM). Values with a p value of <0.01 were considered significant.

Example 4

Gas6 Binding Affinity of Wild-Type, Axl S6-1 and Dead Axl Using Kinetic Exclusion Assay (KinExA)

The kinetic exclusion assay, or KinExA, is an industry standard for measuring extremely tight binding interactions and here is employed in measuring the Gas6-Axl interactions. (See, e.g., Ohmura et al., *Anal. Chem.* 73:3392-3399 (2001).) KinExA was performed on the Ig1 domains of wild-type Axl, Axl S6-1 and the non-binding dead Axl variants. In addition to equilibrium binding affinities, binding kinetics were also experimentally determined using KinExA; results are summarized in Table 7.

TABLE 7

| | Residue no. | | | | | | Gas6 binding affinity | | |
|---|---|---|---|---|---|---|---|---|---|
| | 32 | 59 | 77 | 87 | 92 | 127 | $K_d$ (pM) | $k_{on}$ ($10^7 M^{-1}s^{-1}$) | $k_{off}$ ($10^{-4} s^{-1}$) |
| wt Axl | G | E | T | D | V | G | 32.8 ± 0.63 | 2.1 ± 0.06 | 7.0 ± 0.20 |
| S6-1 | S | | | G | A | R | 2.7 ± 0.05 | 1.6 ± 0.03 | 0.4 ± 0.01 |
| Dead | | R | R | | | | >1 μM | n.d. | n.d. |

Table 7 describes that the resolution of KinExA allowed a determination of the strengths of the Gas6-Axl interactions, with the wild-type interaction having an affinity of 32.8 picomolar. Our engineered Axl variant, S6-1, has greater than a 12-fold improvement in Gas6 binding affinity over wild-type, and has been measured to be 2.7 picomolar. Furthermore, KinExA confirmed that dead Axl possesses no measurable binding affinity to Gas6 up to concentrations of 1 micromolar. Finally, KinExA measurements reaffirmed that improvements in binding affinity are a result of an enhanced, or slower, off-rate.

Determining the Contributions of the Four Point Mutations Found in Axl S6-1.

Axl S6-1, has four mutations from wild-type; G32S, D87G, V92A, and G127R. In an effort to determine whether all four mutations are required to confer superior binding affinity, each mutation was individually placed into wild-type Axl and their affinities and rate constants were determined using KinExA. In an alternative approach to parsing out the contributions of each mutation, all combinations of three of the four mutations found in S6-1 were also made and tested. All of these measurements were done on Axl Ig1 variants. The data is summarized in Table 8.

TABLE 8

| | Residue no. | | | | Gas6 binding affinity | | |
|---|---|---|---|---|---|---|---|
| | 32 | 87 | 92 | 127 | $K_d$ (pM) | $k_{on}$ ($10^7 M^{-1}s^{-1}$) | $k_{off}$ ($10^{-4} s^{-1}$) |
| wt Axl | G | D | V | G | 32.8 ± 0.63 | 2.1 ± 0.06 | 7.0 ± 0.20 |
| wt +32 | S | | | | 38.9 ± 0.80 | 1.9 ± 0.04 | 7.4 ± 0.16 |
| wt +87 | | G | | | 14.1 ± 0.22 | 2.0 ± 0.04 | 2.8 ± 0.05 |
| wt +92 | | | A | | 12.0 ± 0.25 | 1.7 ± 0.05 | 2.1 ± 0.06 |
| wt +127 | | | | R | 32.0 ± 0.78 | 2.3 ± 0.05 | 7.2 ± 0.15 |
| S6-1 −32 | | G | A | R | 7.6 ± 0.17 | 1.8 ± 0.04 | 1.3 ± 0.03 |
| S6-1 −87 | S | | A | R | 8.6 ± 0.25 | 1.7 ± 0.05 | 1.4 ± 0.04 |
| S6-1 −92 | S | G | | R | 13.1 ± 0.36 | 2.1 ± 0.03 | 2.7 ± 0.04 |
| S6-1 −127 | S | G | A | | 4.09 ± 0.09 | 1.9 ± 0.05 | 0.7 ± 0.02 |

The data in Table 8 shows that all four mutations are required to obtain the 2.7 pM binding affinity of Axl S6-1, though removal of the G127R mutation does not substantially reduce the overall affinity by much. These data also outline several additional Axl variants with enhanced binding affinity to Gas6, namely; Axl (D87G), Axl (V92A), Axl (D87G/V92A/G127R), Axl (G32S/V92A/G127R), Axl (G32S/D87G/G127R), and Axl (G32S/D87G/V92A).

Figure 16:
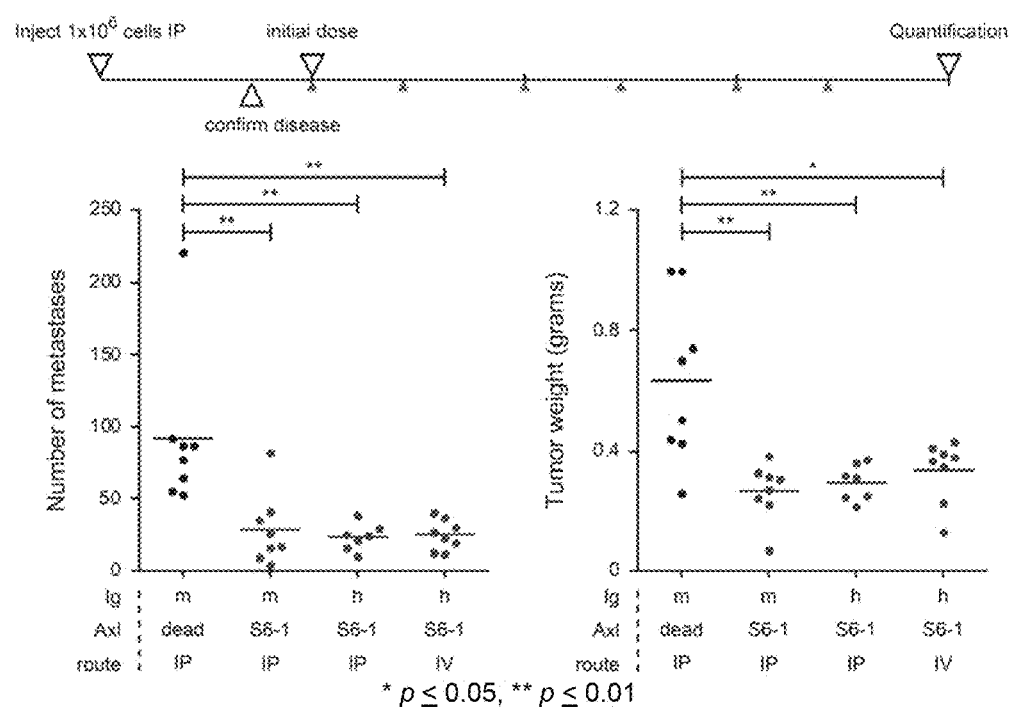
FIG. 16. Skov3 efficacy data. Metastatic disease was quantified by counting all visible metastatic lesions in the peritoneal cavity and excising and weighing all diseased tissue to determine the overall number and weight of metastases and then graphed.

Determining the Binding Affinity of Other Axl Variants of Interest Using KinExA.

After seeing the strong contributions made by D87G and V92A independently, we also measure the affinity the combination of those two mutations. Additionally, there was a single point mutant that arose quite prominently in the sort 5 pool (Table 2 in original filing), A72V, and this variant was explored as well. KinExA was again used to determine Gas6 binding affinity and rate constants of these two Axl variants; data summarized in Table 9.

TABLE 9

| | Res. no. | | | Gas6 binding affinity | | |
|---|---|---|---|---|---|---|
| | 72 | 87 | 92 | $K_d$ (pM) | $k_{on}$ ($10^7 M^{-1}s^{-1}$) | $k_{off}$ ($10^{-4} s^{-1}$) |
| wt Axl | A | D | V | 32.8 ± 0.63 | 2.1 ± 0.06 | 7.0 ± 0.20 |
| wt +72 | V | | | 5.8 ± 0.11 | 1.9 ± 0.04 | 1.1 ± 0.02 |
| wt +87/92 | | G | A | 5.7 ± 0.63 | 2.0 ± 0.07 | 1.2 ± 0.04 |

The data in Table 9 show two additional Axl variants which possess extremely high affinity to Gas6, almost recapitulating the affinity of Axl S6-1. As with all previous affinity enhancements, analysis of the rate constants shows improvements are a result of slower dissociation of the complex.

In Vivo Efficacy of IV Vs IP Dosing and Mouse Vs Human Fc Fusions.

The goal of this experiment was to evaluate whether the ortholog of the Fc domain, (mouse or human) impacts the safety and efficacy profile of Axl S6-1 Fc fusion. In addition, this example also aims to determine whether any differences in safety and efficacy exist when Axl S6-1 Fc is administered intravenously (IV) versus intraperitoneally (IP).

Mice were injected with human ovarian cancer cells (SKOV3) IP, which were allowed to establish for one week. Tumor bearing mice were then randomized into one of four treatment groups, outlined in Table 10.

TABLE 10

| Group | Treatment | n* | Dosage (mg/kg) | Route/schedule | Length |
|---|---|---|---|---|---|
| 1 | Dead Axl $mIgG_{2\alpha}$ | 8 | 10 | IP, twice a week | 6 doses |
| 2 | Axl S6-1 $mIgG_{2\alpha}$ | 8 | 10 | IP, twice a week | 6 doses |
| 3 | Axl S6-1 $hIgG_1$ | 8 | 10 | IP, twice a week | 6 doses |
| 4 | Axl S6-1 $hIgG_1$ | 8 | 10 | IV, twice a week | 6 doses |

Metastatic tumor burden was assessed after 3 weeks of dosing, which corresponds to 28 days post tumor inoculation. Metastatic disease was quantified by counting all visible metastatic lesions in the peritoneal cavity and excising and weighing all diseased tissue to determine the overall number and weight of metastases, respectively. Data for the study is shown in FIG. 16 and Table 11.

TABLE 11

| Group # | Axl variant | Fc ortholog | Route of administration | Number average | SEM | Weight (g) average | SEM |
|---|---|---|---|---|---|---|---|
| 2 | Axl S6-1 | Mouse | IP | 28.75 | 8.80 | 0.27 | 0.03 |
| 4 | Axl S6-1 | Human | IV | 25.13 | 3.66 | 0.33 | 0.04 |

The data from this study allows three major conclusions to be drawn in regards to the safety and efficacy profile of various Axl Fc fusion constructs. This study further describes that Axl S6-1 has potent anti-metastatic affects in vivo. The orthotype of the Fc domain (mouse or human) in the fusion construct does not appear to impact the efficacy of the treatment. The route of administration (IV vs IP) also does not impact therapeutic efficacy.

Example 5

In Vivo Evaluation of Efficacy and Safety of Axl S6-1 Fc Fusion in the Treatment of a Mouse Breast Cancer Xenograft Model Study Objective. The objective of this research is to evaluate the efficacy and safety of Axl S6-1 mIgG2αFc fusion in the treatment of 4T1 mouse breast cancer xenograft model in nude mice.

The Experimental Design is shown in Table 12.

TABLE 12

| Group | Treatment | n* | Dosage (mg/kg) | Route/schedule | Length |
|---|---|---|---|---|---|
| 1 | Dead Axl mIgG$_{2\alpha}$ | 12 | 10 | IV, twice a week | 6 doses |
| 2 | Axl S6-1 mIgG$_{2\alpha}$ | 12 | 1 | IV, twice a week | 6 doses |
| 3 | Axl S6-1 mIgG$_{2\alpha}$ | 12 | 10 | IV, twice a week | 6 doses |

Note:
n*: number of animals;
q.d. dose any time during the day.

Animals. 40-6 week old female *mus musculus* were used in this study. The mice were kept in laminar flow rooms at constant temperature and humidity with 5 animals in each cage. Temperature was kept at 22±3° C. and humidity was 40-80% The cages were made of polycarbonate and were 300 mm×180 mm×150 mm. The bedding material was soft wood, which was changed once per week. Animals had free access to irradiation sterilized dry granule food during the entire study period. Animals had free access to sterile drinking water.

Experimental Methods and Procedures
Cell Culture

4T1—luciferase tumor cells were maintained in vitro as a monolayer culture in RPMI medium supplemented with 10% heat inactivated fetal calf serum, 100 U/ml penicillin and 100 µg/ml streptomycin, and L-glutamine (2 mM) at 37° C. in an atmosphere of 5% $CO_2$ in air. The tumor cells were routinely subcultured twice weekly by trypsin-EDTA treatment. Cells growing in an exponential growth phase were harvested and counted using a Beckman Coulter particle counter prior to tumor inoculation.

Tumor Inoculation

Each mouse was inoculated subcutaneously in the mammary fat pad with 4T1 tumor cells ($5 \times 10^4$) in 0.05 ml of sterile saline for tumor development. Establishment of primary tumors was confirmed 3 days after inoculation by injecting all mice IP with D-luciferin and using bioluminescence imaging to observe the presence 4T1—luciferase tumors. Treatment began 4 days after tumor inoculation. Tumor bearing mice were randomly divided into three groups consisting of 12 animals. The testing articles were administered to the mice according to the predetermined regimen shown in the experiment design table (Table 12).

TABLE 13

Testing Articles and Dosing Solution Preparation

| Compounds | Preparation | Concentration | Storage |
|---|---|---|---|
| Dead Axl mIgG$_{2\alpha}$ | 0.2 µm filter sterilized in phosphate buffered saline | 1.0 mg/ml | 4° C. |
| Axl S6-1 mIgG$_{2\alpha}$ | 0.2 µm filter sterilized in phosphate buffered saline | 0.1 mg/ml | 4° C. |
| Axl S6-1 mIgG$_{2\alpha}$ | 0.2 µm filter sterilized in phosphate buffered saline | 1.0 mg/ml | 4° C. |

*concentrations of testing articles prepared such that injection volumes were constant.

Metastatic Disease

The endpoint was to see if spontaneous 4T1 metastasis to the lungs could be delayed or abolished. Metastatic tumor burden was assessed after three weeks of dosing, 24 days post-tumor inoculation. Metastatic disease was quantified by injecting mice with D– luciferin, sacrificing the mice ten minutes post-injection and using ex vivo bioluminescence imaging to quantify 4T1 tumor cells in the lungs. Furthermore, Taqman® quantitative PCR amplifying the luciferase gene was used to measure metastatic disease in the lungs of each animal.

Statistical Analysis

Figure 17:
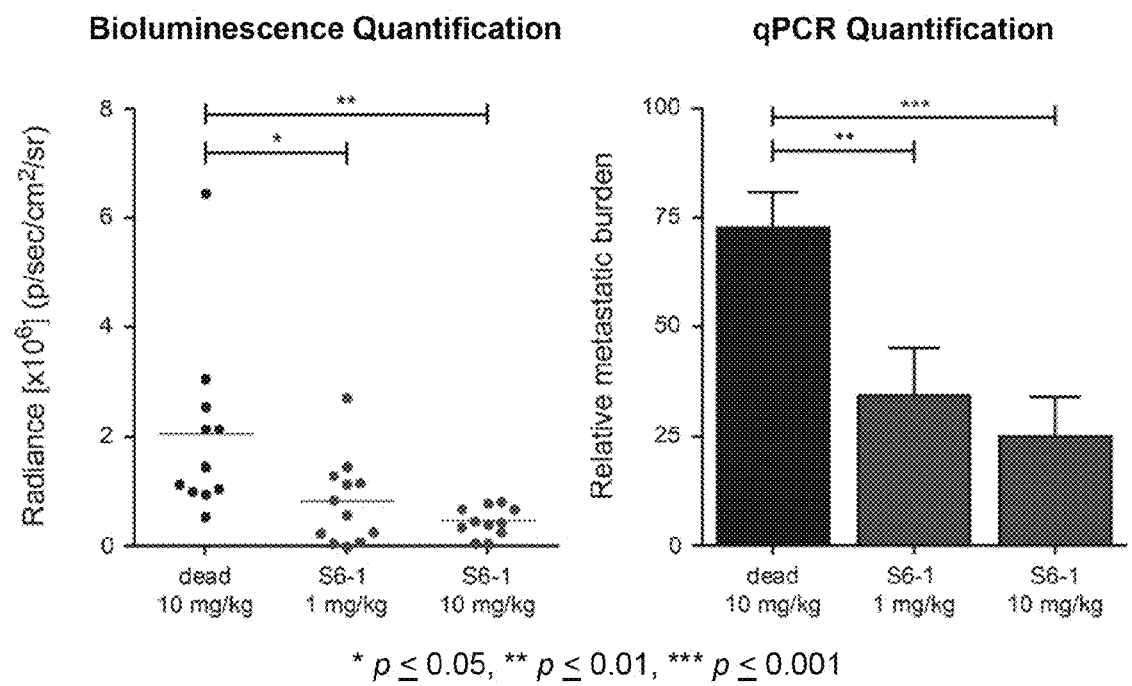
FIG. 17. Metastatic tumor burden in the lungs after three weeks of treatment in the 4T1 mouse breast cancer xenograft model.

Data including the mean and SEM of metastatic disease burden in the lungs is summarized in FIG. 17 and Tables 14 and 15. Statistical analysis of the differences in tumor number and weight among the groups were conducted on the final data obtained. A student t-test was performed to compare final tumor volume and metastatic burden among groups; $p \leq 0.05$ was considered to be statistically significant. Statistical outliers were determined using Grubbs' outlier test.

Metastatic Disease

Quantification of lung metastases 24 days post-inoculation in each of the three treatment groups is summarized in FIG. 17 and Tables 14 and 15.

TABLE 14

Bioluminescence quantification of lung metastases
Radiance [$\times 10^6$] (p/sec/cm$^2$/sr)

| Group # | Axl variant | Dose (mg/kg) | Average | SEM |
|---|---|---|---|---|
| 2 | Axl S6-1 | 1 | 0.81 | 0.23 |

TABLE 15 qPCR quantification of lung metastases
Relative metastatic burden

| Group # | Axl variant | Dose (mg/kg) | Average | SEM |
|---|---|---|---|---|
| 2 | Axl S6-1 | 1 | 33.98 | 10.60 |

Result Summary

In this study, the therapeutic efficacy and safety of the test compound Axl S6-1 mIgG$_{2\alpha}$ was evaluated as a single agent in the treatment of mouse breast cancer using a 4T1—luciferase xenograph model. Results summarizing data describing metastatic tumor burden in the lungs of animals 24 days post-tumor inoculation are shown in FIG. 17 and Tables 14 and 15.

Metastatic Tumor Burden

At 24 days post tumor inoculation, mice were injected IP with D-luciferin and sacrificed ten minutes post-injection. Lungs were excised, bathed in 0.5 mL of PBS containing D-luciferin and bioluminescence images were immediately obtained using an IVIS 200 imaging system. The mean metastatic burden in the lungs of mice receiving dead-Axl mIgG$_{2\alpha}$ was 2,042×10$^6$ (p/sec/cm$^2$/sr) as quantified by bioluminescence imaging. Treatment with the test compound Axl S6-1 mIgG$_{2\alpha}$ at 1 or 10 mg/kg resulted in significant antitumor activity with metastatic burdens of 814×10$^6$ and 450×10$^6$ (p/sec/cm$^2$/sr), respectively (p≤0.05 and p≤0.01, respectively, compared to dead-Axl mIgG$_{2\alpha}$).

After imaging, whole lungs were weighed and homogenized to isolate genomic DNA for metastatic burden analysis. Taqman® quantitative PCR was used to amplify the firefly luciferase gene, while expression of vimentin was used as a reference gene. By comparing the Ct value of vimentin and luciferase (ΔCt), a score for relative bumor burden was calculated using the formula:

$$\text{Relative metastatic burden} = 10{,}000 * \frac{1^{\Delta Ct}}{2}$$

Signals arising from cycle numbers higher than 42 were considered as background as negative control samples without DNA begin producing background signal after this many cycles.

The mean relative metastatic burden in the lungs of mice receiving dead-Axl mIgG$_{2\alpha}$ was 72 as quantified by qPCR. Treatment with the test compound Axl S6-1 mIgG$_{2\alpha}$ at 1 or 10 mg/kg resulted in significantly reduced metastatic burdens of 11 and 9, respectively (p≤0.01 and p≤0.001, respectively, compared to dead-Axl mIgG$_{2\alpha}$).

Regarding the safety profile, the test compound Axl S6-1 mIgG$_{2\alpha}$ was tolerated well by the tumor-bearing animals with no observable weight loss. No gross clinical abnormalities were observed in these animals during the treatment period.

In summary, the test compound Axl S6-1 mIgG$_{2\alpha}$, as a single agent produced a significant antitumor activity in the treatment of a mouse breast cancer xenograft model. The test compound significantly decreased metastasis to the lungs as compared to the control group. The test compound has a very safe profile and was well tolerated by the tumor-bearing animals at the used dose and treatment schedule.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. An isolated soluble AXL variant polypeptide, wherein said polypeptide lacks the AXL transmembrane domain and has an amino acid substitution relative to the wild-type AXL sequence (SEQ ID NO.1) of alanine 72 to valine, and wherein said substitution increases the affinity of the AXL polypeptide binding to GAS6.

2. An isolated soluble AXL variant polypeptide, wherein said polypeptide lacks the AXL transmembrane domain and has a s set of amino acid substitutions relative to SEQ ID NO.1 wherein glycine 32 residue is replaced with a serine residue, aspartic acid 87 residue is replaced with a glycine residue, valine 92 residue is replaced with an alanine residue, glycine 127 residue is replaced with an arginine residue and alanine 72 residue is replaced with a valine residue.

3. The soluble AXL variant polypeptide of claim 1 or claim 2, wherein to polypeptide is a fusion protein comprising an Fc domain.

4. The soluble AXL variant polypeptide of claim 1 or claim 2, wherein said soluble AXL variant polypeptide exhibits an affinity to GAS6 that is at least about 10-fold stronger or at least about 20 fold stronger than the affinity of the wild-type AXL polypeptide.

5. The soluble AXL variant polypeptide of claim 1 or claim 2, wherein said soluble AXL variant polypeptide inhibits binding between wild-type AXL polypeptide and a GAS6 protein in vivo or in vitro.

6. A pharmaceutical composition comprising a therapeutically effective amount a soluble AXL variant polypeptide of claim 1 or claim 2 and a pharmaceutically acceptable excipient.

7. The pharmaceutical composition of claim 6, further comprising at least one cytotoxic agent or a pharmaceutically acceptable excipient or a combination thereof.

* * * * *

SEQUENCE LISTING

```
<160> NUMBER OF SEQ ID NOS: 17

<210> SEQ ID NO 1
<211> LENGTH: 887
<212> TYPE: PRT
<213> ORGANISM: H. sapiens

<400> SEQUENCE: 1

Met Gly Arg Val Pro Leu Ala Trp Cys Leu Ala Leu Cys Gly Trp Ala
 1               5                  10                  15

Cys Met Ala Pro Arg Gly Thr Gln Ala Glu Glu Ser Pro Phe Val Gly
            20                  25                  30

Asn Pro Gly Asn Ile Thr Gly Ala Arg Gly Leu Thr Gly Thr Leu Arg
        35                  40                  45

Cys Gln Leu Gln Val Gln Gly Glu Pro Pro Glu Val His Trp Leu Arg
    50                  55                  60

Asp Gly Gln Ile Leu Glu Leu Ala Asp Ser Thr Gln Thr Gln Val Pro
65                  70                  75                  80

Leu Gly Glu Asp Glu Gln Asp Asp Trp Ile Val Val Ser Gln Leu Arg
                85                  90                  95

Ile Thr Ser Leu Gln Leu Ser Asp Thr Gly Gln Tyr Gln Cys Leu Val
            100                 105                 110

Phe Leu Gly His Gln Thr Phe Val Ser Gln Pro Gly Tyr Val Gly Leu
        115                 120                 125
```

-continued

Glu Gly Leu Pro Tyr Phe Leu Glu Glu Pro Glu Asp Arg Thr Val Ala
130                 135                 140

Ala Asn Thr Pro Phe Asn Leu Ser Cys Gln Ala Gln Gly Pro Pro Glu
145                 150                 155                 160

Pro Val Asp Leu Leu Trp Leu Gln Asp Ala Val Pro Leu Ala Thr Ala
                165                 170                 175

Pro Gly His Gly Pro Gln Arg Ser Leu His Val Pro Gly Leu Asn Lys
            180                 185                 190

Thr Ser Ser Phe Ser Cys Glu Ala His Asn Ala Lys Gly Val Thr Thr
        195                 200                 205

Ser Arg Thr Ala Thr Ile Thr Val Leu Pro Gln Gln Pro Arg Asn Leu
210                 215                 220

His Leu Val Ser Arg Gln Pro Thr Glu Leu Glu Val Ala Trp Thr Pro
225                 230                 235                 240

Gly Leu Ser Gly Ile Tyr Pro Leu Thr His Cys Thr Leu Gln Ala Val
                245                 250                 255

Leu Ser Asp Asp Gly Met Gly Ile Gln Ala Gly Glu Pro Asp Pro Pro
            260                 265                 270

Glu Glu Pro Leu Thr Ser Gln Ala Ser Val Pro Pro His Gln Leu Arg
        275                 280                 285

Leu Gly Ser Leu His Pro His Thr Pro Tyr His Ile Arg Val Ala Cys
290                 295                 300

Thr Ser Ser Gln Gly Pro Ser Ser Trp Thr His Trp Leu Pro Val Glu
305                 310                 315                 320

Thr Pro Glu Gly Val Pro Leu Gly Pro Glu Asn Ile Ser Ala Thr
                325                 330                 335

Arg Asn Gly Ser Gln Ala Phe Val His Trp Gln Glu Pro Arg Ala Pro
            340                 345                 350

Leu Gln Gly Thr Leu Leu Gly Tyr Arg Leu Ala Tyr Gln Gly Gln Asp
        355                 360                 365

Thr Pro Glu Val Leu Met Asp Ile Gly Leu Arg Gln Glu Val Thr Leu
370                 375                 380

Glu Leu Gln Gly Asp Gly Ser Val Ser Asn Leu Thr Val Cys Val Ala
385                 390                 395                 400

Ala Tyr Thr Ala Ala Gly Asp Gly Pro Trp Ser Leu Pro Val Pro Leu
                405                 410                 415

Glu Ala Trp Arg Pro Gly Gln Ala Gln Pro Val His Gln Leu Val Lys
            420                 425                 430

Glu Pro Ser Thr Pro Ala Phe Ser Trp Pro Trp Trp Tyr Val Leu Leu
        435                 440                 445

Gly Ala Val Val Ala Ala Cys Val Leu Ile Leu Ala Leu Phe Leu
450                 455                 460

Val His Arg Arg Lys Lys Glu Thr Arg Tyr Gly Glu Val Phe Glu Pro
465                 470                 475                 480

Thr Val Glu Arg Gly Glu Leu Val Val Arg Tyr Arg Val Arg Lys Ser
                485                 490                 495

Tyr Ser Arg Arg Thr Thr Glu Ala Thr Leu Asn Ser Leu Gly Ile Ser
            500                 505                 510

Glu Glu Leu Lys Glu Lys Leu Arg Asp Val Met Val Asp Arg His Lys
        515                 520                 525

Val Ala Leu Gly Lys Thr Leu Gly Glu Gly Glu Phe Gly Ala Val Met
530                 535                 540

Glu Gly Gln Leu Asn Gln Asp Asp Ser Ile Leu Lys Val Ala Val Lys

```
            545                 550                 555                 560
        Thr Met Lys Ile Ala Ile Cys Thr Arg Ser Glu Leu Glu Asp Phe Leu
                        565                 570                 575
        Ser Glu Ala Val Cys Met Lys Glu Phe Asp His Pro Asn Val Met Arg
                        580                 585                 590
        Leu Ile Gly Val Cys Phe Gln Gly Ser Glu Arg Glu Ser Phe Pro Ala
                        595                 600                 605
        Pro Val Val Ile Leu Pro Phe Met Lys His Gly Asp Leu His Ser Phe
                        610                 615                 620
        Leu Leu Tyr Ser Arg Leu Gly Asp Gln Pro Val Tyr Leu Pro Thr Gln
        625                 630                 635                 640
        Met Leu Val Lys Phe Met Ala Asp Ile Ala Ser Gly Met Glu Tyr Leu
                        645                 650                 655
        Ser Thr Lys Arg Phe Ile His Arg Asp Leu Ala Ala Arg Asn Cys Met
                        660                 665                 670
        Leu Asn Glu Asn Met Ser Val Cys Val Ala Asp Phe Gly Leu Ser Lys
                        675                 680                 685
        Lys Ile Tyr Asn Gly Asp Tyr Tyr Arg Gln Gly Arg Ile Ala Lys Met
                        690                 695                 700
        Pro Val Lys Trp Ile Ala Ile Glu Ser Leu Ala Asp Arg Val Tyr Thr
        705                 710                 715                 720
        Ser Lys Ser Asp Val Trp Ser Phe Gly Val Thr Met Trp Glu Ile Ala
                        725                 730                 735
        Thr Arg Gly Gln Thr Pro Tyr Pro Gly Val Glu Asn Ser Glu Ile Tyr
                        740                 745                 750
        Asp Tyr Leu Arg Gln Gly Asn Arg Leu Lys Gln Pro Ala Asp Cys Leu
                        755                 760                 765
        Asp Gly Leu Tyr Ala Leu Met Ser Arg Cys Trp Glu Leu Asn Pro Gln
                        770                 775                 780
        Asp Arg Pro Ser Phe Thr Glu Leu Arg Glu Asp Leu Glu Asn Thr Leu
        785                 790                 795                 800
        Lys Ala Leu Pro Pro Ala Gln Glu Pro Asp Glu Ile Leu Tyr Val Asn
                        805                 810                 815
        Met Asp Glu Gly Gly Tyr Pro Glu Pro Pro Gly Ala Ala Gly Gly
                        820                 825                 830
        Ala Asp Pro Pro Thr Gln Pro Asp Pro Lys Asp Ser Cys Ser Cys Leu
                        835                 840                 845
        Thr Ala Ala Glu Val His Pro Ala Gly Arg Tyr Val Leu Cys Pro Ser
        850                 855                 860
        Thr Thr Pro Ser Pro Ala Gln Pro Ala Asp Arg Gly Ser Pro Ala Ala
        865                 870                 875                 880
        Pro Gly Gln Glu Asp Gly Ala
                        885

<210> SEQ ID NO 2
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 2

Arg Met Phe Ser Gly Thr Pro Val Ile Arg Leu Arg Phe Lys Arg Leu
 1               5                  10                  15

Gln Pro Thr
```

-continued

```
<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Val Gly Arg Val Thr Ser Ser Gly Pro
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 4

Arg Asn Leu Val Ile Lys Val Asn
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Asp Ala Val Met Lys Ile Ala Val Ala
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 6

Glu Arg Gly Leu Tyr His Leu Asn Leu Thr Val Gly Ile Pro Phe
1               5                   10                  15

His

<210> SEQ ID NO 7
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 7

Trp Leu Asn Gly Glu Asp Thr Thr Ile Gln Glu Thr Val Lys Val Asn
1               5                   10                  15

Thr Arg Met

<210> SEQ ID NO 8
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 8
```

```
gatttggaga acacactga                                                  19

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 9
aattgtacta cacaaaagta c                                               21

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
gcccgaagcg tttactttga                                                 20

<210> SEQ ID NO 11
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 11
tccattattc ctagctgcgg tatc                                            24

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 12
gtgggcaacc cagggaatat c                                               21

<210> SEQ ID NO 13
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 13
gtactgtccc gtgtcggaaa g                                               21

<210> SEQ ID NO 14
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 14
atggggaagg tgaaggtcg                                                  19

<210> SEQ ID NO 15
<211> LENGTH: 22
<212> TYPE: DNA
```

```
<213> ORGANISM: Artificial Sequence
<220> FEATURE:
<223> OTHER INFORMATION: Synthetic Oligonucleotide

<400> SEQUENCE: 15
ggggtcattg atggcaacaa ta                                               22

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
gccccagaca ggtgatcttg                                                  20

<210> SEQ ID NO 17
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 17
gcttgcgagg gaagaagttg t                                                21
```